United States Patent
Vendely et al.

(10) Patent No.: US 11,708,652 B2
(45) Date of Patent: Jul. 25, 2023

(54) KNITTED TISSUE SCAFFOLDS

(71) Applicant: Cilag GmbH International, Zug (CH)

(72) Inventors: Michael J. Vendely, Lebanon, OH (US); Victoria Dalessandro, Scotch Plains, NJ (US); Jason L. Harris, Lebanon, OH (US); Frederick E. Shelton, IV, Hillsboro, OH (US)

(73) Assignee: Cilag GmbH International, Zug (CH)

( * ) Notice: Subject to any disclaimer, the term of this patent is extended or adjusted under 35 U.S.C. 154(b) by 0 days.

(21) Appl. No.: 17/966,024

(22) Filed: Oct. 14, 2022

(65) Prior Publication Data

US 2023/0109512 A1    Apr. 6, 2023

Related U.S. Application Data

(63) Continuation of application No. 17/208,280, filed on Mar. 22, 2021, now Pat. No. 11,512,415, which is a continuation of application No. 15/901,103, filed on Feb. 21, 2018, now Pat. No. 10,982,360.

(51) Int. Cl.
| | | |
|---|---|---|
| *D04B 21/20* | (2006.01) | |
| *A61B 17/072* | (2006.01) | |
| *D04B 21/16* | (2006.01) | |
| *D04B 23/10* | (2006.01) | |

(52) U.S. Cl.
CPC ........ *D04B 21/20* (2013.01); *A61B 17/07292* (2013.01); *D04B 21/16* (2013.01); *D04B 23/10* (2013.01); *A61B 2017/07271* (2013.01)

(58) Field of Classification Search
CPC ........ D04B 21/20; D04B 21/16; D04B 23/10; A61B 17/07292; A61B 2017/07272; A61B 17/064
See application file for complete search history.

(56) References Cited

U.S. PATENT DOCUMENTS

| | | |
|---|---|---|
| D297,764 S | 9/1988 | Hunt et al. |
| 4,892,244 A | 1/1990 | Fox et al. |
| RE34,519 E | 1/1994 | Fox et al. |
| 5,542,594 A | 8/1996 | McKean et al. |
| 5,690,675 A | 11/1997 | Sawyer et al. |
| 5,698,213 A | 12/1997 | Jamiolkowski et al. |
| 5,700,583 A | 12/1997 | Jamiolkowski et al. |
| 5,814,057 A | 9/1998 | Oi et al. |
| 6,147,135 A | 11/2000 | Yuan et al. |

(Continued)

FOREIGN PATENT DOCUMENTS

| | | |
|---|---|---|
| EP | 0449431 A2 | 10/1991 |
| EP | 2008595 A2 | 12/2008 |

(Continued)

OTHER PUBLICATIONS

U.S. Appl. No. 16/119,292, filed Aug. 31, 2018, Adjunct Materials and Methods of Using Same in Surgical Methods for Tissue Sealing.

(Continued)

*Primary Examiner* — Danny Worrell
(74) *Attorney, Agent, or Firm* — Mintz Levin Cohn Ferris Glovsky and Popeo, P.C.

(57) ABSTRACT

Staple cartridge assemblies for use with surgical stapling instruments and methods for manufacturing the same are provided. Scaffolds for use with a surgical staple cartridge and methods for manufacturing the same are also provided.

6 Claims, 12 Drawing Sheets
(3 of 12 Drawing Sheet(s) Filed in Color)

(56) References Cited

U.S. PATENT DOCUMENTS

| | | |
|---|---|---|
| 6,325,810 B1 | 12/2001 | Hamilton et al. |
| 6,736,823 B2 | 5/2004 | Darois et al. |
| 7,143,924 B2 | 12/2006 | Scirica et al. |
| 7,143,925 B2 | 12/2006 | Shelton, IV et al. |
| 7,192,604 B2 | 3/2007 | Brown et al. |
| 7,641,091 B2 | 1/2010 | Olson et al. |
| 7,772,352 B2 | 8/2010 | Bezwada |
| 8,317,070 B2 | 11/2012 | Hueil et al. |
| 8,393,514 B2 | 3/2013 | Shelton, IV et al. |
| 8,551,058 B2 | 10/2013 | Measamer et al. |
| 8,590,762 B2 | 11/2013 | Hess et al. |
| 9,307,965 B2 | 4/2016 | Ming et al. |
| 9,332,984 B2 | 5/2016 | Weaner et al. |
| 9,445,808 B2 | 9/2016 | Woodard et al. |
| 9,615,826 B2 | 4/2017 | Shelton, IV et al. |
| 9,700,311 B2 | 7/2017 | Shelton, IV et al. |
| 9,801,630 B2 | 10/2017 | Harris et al. |
| 9,826,965 B2 | 11/2017 | Stokes et al. |
| 9,848,871 B2 | 12/2017 | Harris et al. |
| 9,913,642 B2 | 3/2018 | Leimbach et al. |
| 9,913,646 B2 | 3/2018 | Shelton, IV |
| 9,924,944 B2 | 3/2018 | Shelton, IV et al. |
| 9,924,946 B2 | 3/2018 | Vendely et al. |
| 9,936,950 B2 | 4/2018 | Shelton, IV et al. |
| 9,936,954 B2 | 4/2018 | Shelton, IV et al. |
| 10,028,744 B2 | 7/2018 | Shelton, IV et al. |
| 10,052,104 B2 | 8/2018 | Shelton, IV et al. |
| D831,209 S | 10/2018 | Huitema et al. |
| D836,198 S | 12/2018 | Harris et al. |
| 10,166,026 B2 | 1/2019 | Shelton, IV et al. |
| 10,172,611 B2 | 1/2019 | Shelton, IV et al. |
| 10,172,616 B2 | 1/2019 | Murray et al. |
| 10,206,686 B2 | 2/2019 | Swayze et al. |
| 10,271,849 B2 | 4/2019 | Vendely et al. |
| 10,390,828 B2 | 8/2019 | Vendely et al. |
| 10,426,481 B2 | 10/2019 | Aronhalt et al. |
| 10,441,285 B2 | 10/2019 | Shelton, IV et al. |
| 10,456,129 B2 | 10/2019 | Shelton, IV et al. |
| 10,610,226 B2 | 4/2020 | Shelton, IV et al. |
| D885,574 S | 5/2020 | Shelton, IV et al. |
| 10,682,140 B2 | 6/2020 | Ingmanson et al. |
| 10,695,061 B2 | 6/2020 | Vendely et al. |
| 10,952,724 B2 | 3/2021 | Shelton, IV et al. |
| 10,959,721 B2 | 3/2021 | Shelton, IV et al. |
| 10,966,713 B2 | 4/2021 | Shelton, IV et al. |
| 10,966,722 B2 | 4/2021 | Shelton, IV et al. |
| 10,980,533 B2 | 4/2021 | Shelton, IV et al. |
| 10,982,360 B2 | 4/2021 | Vendely et al. |
| 11,026,686 B2 | 6/2021 | Aranyi |
| 11,155,946 B2 | 10/2021 | Vendely et al. |
| D940,318 S | 1/2022 | Shelton, IV et al. |
| 11,272,932 B2 | 3/2022 | Aranyi |
| 11,446,027 B2 | 9/2022 | Harris et al. |
| 11,512,415 B2 | 11/2022 | Vendely et al. |
| 2005/0059997 A1 | 3/2005 | Bauman et al. |
| 2005/0245965 A1 | 11/2005 | Orban et al. |
| 2006/0084930 A1 | 4/2006 | Dhanaraj et al. |
| 2006/0257458 A1 | 11/2006 | Gorman et al. |
| 2008/0003913 A1 | 1/2008 | Vinson et al. |
| 2008/0140115 A1 | 6/2008 | Stopek |
| 2009/0001122 A1 | 1/2009 | Prommersberger et al. |
| 2009/0090763 A1 | 4/2009 | Zemlok et al. |
| 2009/0234193 A1 | 9/2009 | Weisenburgh et al. |
| 2009/0270686 A1 | 10/2009 | Duke et al. |
| 2010/0023056 A1 | 1/2010 | Johansson et al. |
| 2010/0036441 A1 | 2/2010 | Procter |
| 2011/0087279 A1 | 4/2011 | Shah et al. |
| 2011/0192882 A1 | 8/2011 | Hess et al. |
| 2012/0024934 A1 | 2/2012 | Shelton, IV et al. |
| 2012/0080335 A1 | 4/2012 | Shelton, IV et al. |
| 2012/0080344 A1 | 4/2012 | Shelton, IV |
| 2012/0083835 A1 | 4/2012 | Shelton, IV et al. |
| 2012/0187179 A1 | 7/2012 | Gleiman |
| 2012/0241496 A1 | 9/2012 | Mandakolathur et al. |
| 2012/0241502 A1 | 9/2012 | Aldridge et al. |
| 2012/0253298 A1 | 10/2012 | Henderson et al. |
| 2013/0013074 A1 | 1/2013 | Shikinami |
| 2013/0112731 A1 | 5/2013 | Hodgkinson |
| 2013/0112733 A1 | 5/2013 | Aranyi et al. |
| 2013/0146642 A1 | 6/2013 | Shelton, IV et al. |
| 2013/0153641 A1 | 6/2013 | Shelton, IV et al. |
| 2013/0161374 A1 | 6/2013 | Swayze et al. |
| 2013/0161375 A1 | 6/2013 | Huitema et al. |
| 2013/0256365 A1 | 10/2013 | Shelton, IV et al. |
| 2013/0256372 A1 | 10/2013 | Baxter et al. |
| 2013/0256376 A1 | 10/2013 | Barton et al. |
| 2013/0256377 A1 | 10/2013 | Schmid et al. |
| 2013/0317526 A1 | 11/2013 | Mortarino |
| 2014/0158741 A1 | 6/2014 | Woodard et al. |
| 2014/0158742 A1 | 6/2014 | Stopek et al. |
| 2014/0205637 A1 | 7/2014 | Widenhouse et al. |
| 2014/0224686 A1 | 8/2014 | Aronhalt et al. |
| 2014/0224857 A1 | 8/2014 | Schmid |
| 2014/0277575 A1 | 9/2014 | Landgrebe et al. |
| 2015/0034696 A1 | 2/2015 | Shelton, IV et al. |
| 2015/0099098 A1 | 4/2015 | Bahukudumbi et al. |
| 2015/0099140 A1 | 4/2015 | Amata et al. |
| 2015/0099410 A1 | 4/2015 | Bahukudumbi et al. |
| 2015/0108199 A1 | 4/2015 | Shelton, IV et al. |
| 2015/0134076 A1 | 5/2015 | Shelton, IV et al. |
| 2015/0134077 A1 | 5/2015 | Shelton, IV et al. |
| 2015/0173756 A1 | 6/2015 | Baxter et al. |
| 2015/0196299 A1 | 7/2015 | Swayze et al. |
| 2015/0272575 A1 | 10/2015 | Leimbach et al. |
| 2015/0297222 A1 | 10/2015 | Huitema et al. |
| 2015/0313594 A1 | 11/2015 | Shelton, IV et al. |
| 2015/0351753 A1 | 12/2015 | Shelton, IV et al. |
| 2015/0351754 A1 | 12/2015 | Harris et al. |
| 2015/0351758 A1 | 12/2015 | Shelton, IV et al. |
| 2016/0000430 A1 | 1/2016 | Ming et al. |
| 2016/0106427 A1 | 4/2016 | Shelton, IV et al. |
| 2016/0174974 A1 | 6/2016 | Schmid et al. |
| 2017/0055981 A1 | 3/2017 | Vendely et al. |
| 2017/0056000 A1 | 3/2017 | Nalagatla et al. |
| 2017/0056566 A1 | 3/2017 | Shelton et al. |
| 2017/0086827 A1 | 3/2017 | Vendely et al. |
| 2017/0086829 A1 | 3/2017 | Vendely et al. |
| 2017/0086835 A1 | 3/2017 | Harris et al. |
| 2017/0086837 A1 | 3/2017 | Vendely et al. |
| 2017/0086838 A1 | 3/2017 | Harris et al. |
| 2017/0086841 A1 | 3/2017 | Vendely et al. |
| 2017/0086843 A1 | 3/2017 | Vendely et al. |
| 2017/0119380 A1 | 5/2017 | Dalessandro et al. |
| 2017/0216535 A1 | 8/2017 | Mao |
| 2017/0231633 A1 | 8/2017 | Marczyk et al. |
| 2018/0235626 A1 | 8/2018 | Shelton, IV et al. |
| 2019/0038280 A1 | 2/2019 | Shelton, IV et al. |
| 2019/0059889 A1 | 2/2019 | Shelton, IV et al. |
| 2019/0254659 A1 | 8/2019 | Harris et al. |
| 2019/0254664 A1 | 8/2019 | Vendely et al. |
| 2019/0254665 A1 | 8/2019 | Vendely et al. |
| 2019/0254666 A1 | 8/2019 | Vendely et al. |
| 2019/0254667 A1 | 8/2019 | Vendely et al. |
| 2019/0254668 A1 | 8/2019 | Vendely et al. |
| 2019/0254669 A1 | 8/2019 | Shelton et al. |
| 2019/0298338 A1 | 10/2019 | Vendely et al. |
| 2020/0197006 A1 | 6/2020 | Shelton, IV et al. |
| 2020/0205806 A1 | 7/2020 | Shelton, IV et al. |
| 2021/0177418 A1 | 6/2021 | Shelton, IV et al. |
| 2021/0277555 A1 | 9/2021 | Vendely et al. |
| 2021/0315575 A1 | 10/2021 | Aranyi |
| 2021/0401433 A1 | 12/2021 | Freidel et al. |
| 2022/0015764 A1 | 1/2022 | Shelton, IV et al. |
| 2022/0039797 A1 | 2/2022 | Shelton, IV et al. |
| 2022/0133319 A1 | 5/2022 | Shelton, IV et al. |
| 2022/0133320 A1 | 5/2022 | Shelton, IV et al. |
| 2022/0133321 A1 | 5/2022 | Shelton, IV et al. |
| 2022/0160353 A1 | 5/2022 | Harris et al. |
| 2022/0160354 A1 | 5/2022 | Harris et al. |
| 2022/0160357 A1 | 5/2022 | Harris et al. |

(56) References Cited

U.S. PATENT DOCUMENTS

| | | | |
|---|---|---|---|
| 2022/0160359 A1 | 5/2022 | Harris et al. | |
| 2022/0160360 A1 | 5/2022 | Harris et al. | |

FOREIGN PATENT DOCUMENTS

| | | | |
|---|---|---|---|
| EP | 2353545 A1 | 8/2011 | |
| EP | 2644121 A2 | 10/2013 | |
| EP | 2724734 A2 | 4/2014 | |
| EP | 2954855 A1 | 12/2015 | |
| EP | 2954857 A1 | 12/2015 | |
| EP | 3135222 A1 | 3/2017 | |
| EP | 3150143 A1 | 4/2017 | |
| EP | 3162384 A1 | 5/2017 | |
| EP | 3275378 A1 | 1/2018 | |
| EP | 3363386 A1 | 8/2018 | |
| WO | 2014016819 A1 | 1/2014 | |
| WO | 2015191277 A2 | 12/2015 | |

OTHER PUBLICATIONS

U.S. Appl. No. 16/806,252, filed Mar. 2, 2020, Adjunct Materials and Methods of Using Same in Surgical Methods for Tissue Sealing.
U.S. Appl. No. 16/806,262, filed Mar. 2, 2020, Adjunct Materials and Methods of Using Same in Surgical Methods for Tissue Sealing.
U.S. Appl. No. 17/181,268, filed Feb. 22, 2021, Adjunct Materials and Methods of Using Same in Surgical Methods for Tissue Sealing.
U.S. Appl. No. 17/381,892, filed Jul. 21, 2021, Adjunct Materials and Methods of Using Same in Surgical Methods for Tissue Sealing.
U.S. Appl. No. 17/381,988, filed Jul. 21, 2021, Adjunct Materials and Methods of Using Same in Surgical Methods for Tissue Sealing.
U.S. Appl. No. 17/523,657, filed Nov. 10, 2021, Adjunct Materials and Methods of Using Same in Surgical Methods for Tissue Sealing.
U.S. Appl. No. 17/523,664, filed Nov. 10, 2021, Adjunct Materials and Methods of Using Same in Surgical Methods for Tissue Sealing.
U.S. Appl. No. 17/523,672, filed Nov. 10, 2021, Adjunct Materials and Methods of Using Same in Surgical Methods for Tissue Sealing.
U.S. Appl. No. 17/980,012, filed Nov. 3, 2022, Adjunct Materials and Methods of Using Same in Surgical Methods for Tissue Sealing.
U.S. Appl. No. 17/208,280, filed Mar. 22, 2021, Knitted Tissue Scaffolds.
U.S. Appl. No. 29/732,706, filed Apr. 27, 2020, Knitted Tissue Scaffolds.
U.S. Appl. No. 29/819,905, filed Dec. 17, 2021, Knitted Tissue Scaffolds.
U.S. Appl. No. 15/901,103, filed Feb. 21, 2018, Knitted Tissue Scaffolds.
U.S. Appl. No. 15/901,245, filed Feb. 21, 2018, Knitted Tissue Scaffolds.
U.S. Appl. No. 15/901,613, filed Feb. 21, 2018, Knitted Tissue Scaffolds.
U.S. Appl. No. 15/901,632, filed Feb. 21, 2018, Knitted Tissue Scaffolds.
U.S. Appl. No. 15/901,647, filed Feb. 21, 2018, Knitted Tissue Scaffolds.
U.S. Appl. No. 15/901,668, filed Feb. 21, 2018, Knitted Tissue Scaffolds.
U.S. Appl. No. 29/637,760, filed Feb. 21, 2018, Knitted Tissue Scaffolds.
U.S. Appl. No. 17/104,413, filed Nov. 25, 2020, Compressible Knitted Adjuncts with Finished Edges.
U.S. Appl. No. 17/104,436, filed Nov. 25, 2020, Compressible Knitted Adjuncts with Finished Edges.
U.S. Appl. No. 17/104,463, filed Nov. 25, 2020, Compressible Knitted Adjuncts with Finished Edges.
U.S. Appl. No. 17/104,473, filed Nov. 25, 2020, Compressible Knitted Adjuncts with Varying Interconnections.
U.S. Appl. No. 17/104,488, filed Nov. 25, 2020, Compressible Knitted Adjuncts with Varying Fiber Features.
Extended European Search Report eceived for EP Application No. EP 21156060.2, dated Sep. 20, 2021, 11 pages.
Extended European Search Report received for EP Application No. 15171455.7, dated Sep. 30, 2015, 5 pages.
International Search Report and Written Opinion received for PCT Application No. PCT/IB2019/050505, dated Jun. 4, 2019, 11 pages.
International Search Report and Written Opinion received for PCT Application No. PCT/IB2019/050501, dated Jul. 31, 2019, 22 pages.
International Search Report and Written Opinion received for PCT Application No. PCT/IB2019/050502, dated Aug. 20, 2019, 20 pages.
International Search Report and Written Opinion received for PCT Application No. PCT/IB2019/050503, dated May 21, 2019, 12 pages.
International Search Report and Written Opinion received for PCT Application No. PCT/IB2019/050504, dated Jun. 4, 2019, 12 pages.
International Search Report and Written Opinion received for PCT Application No. PCT/IB2019/050506, dated Jun. 4, 2019, 11 pages.
Partial European Search Report received for EP Application No. 19158395.4, dated May 14, 2019, 8 pages.
Alexei, Donai (Aug. 9, 2018) "How to Stop Fabric Edges From Fraying Using No-Sew Finishing Techniques.", URL https://www.doinaalexei.com/beginnersewingtutorialblog/how-to-stop-fabric-edges-from-fraying-using-no-sew-finishing-techniques, retrieved on Nov. 22, 2022, 26 pages.
Baker et al. (Nov. 2004) "The Science of Stapling and Leaks", Obesity Surgery, 14:1290-1298.
Chen et al. (2013) "Elastomeric Biomaterials for Tissue Engineering", Progress in Polymer Science, 38(3-4):584-671.
Flores, Jessica (Nov. 12, 2022) "10 Types of Edge Finishes in Sewing", https://sewingmachinebuffs.com/10-types-of-edge-finishes-in-sewing/, 23 pages.
Lim et al. (May 2012) "Fabrication and Evaluation of Poly(epsilon-Caprolactone)/Silk Fibroin Blend Nanofibrous Scaffold", Biopolymers, 97(5):265-275.
Ye et al. (2008) "Development of the Warp Knitted Spacer Fabrics for Cushion Applications", Journal of Industrial Textiles, 37(3):213-223.
Zhao et al. (Nov. 2007) "Biodegradable Fibrous Scaffolds Composed of Gelatin Coated Poly($\epsilon$-caprolactone) Prepared by Coaxial Electrospinning", Journal of Biomedical Materials Research, 83(2):372-382.

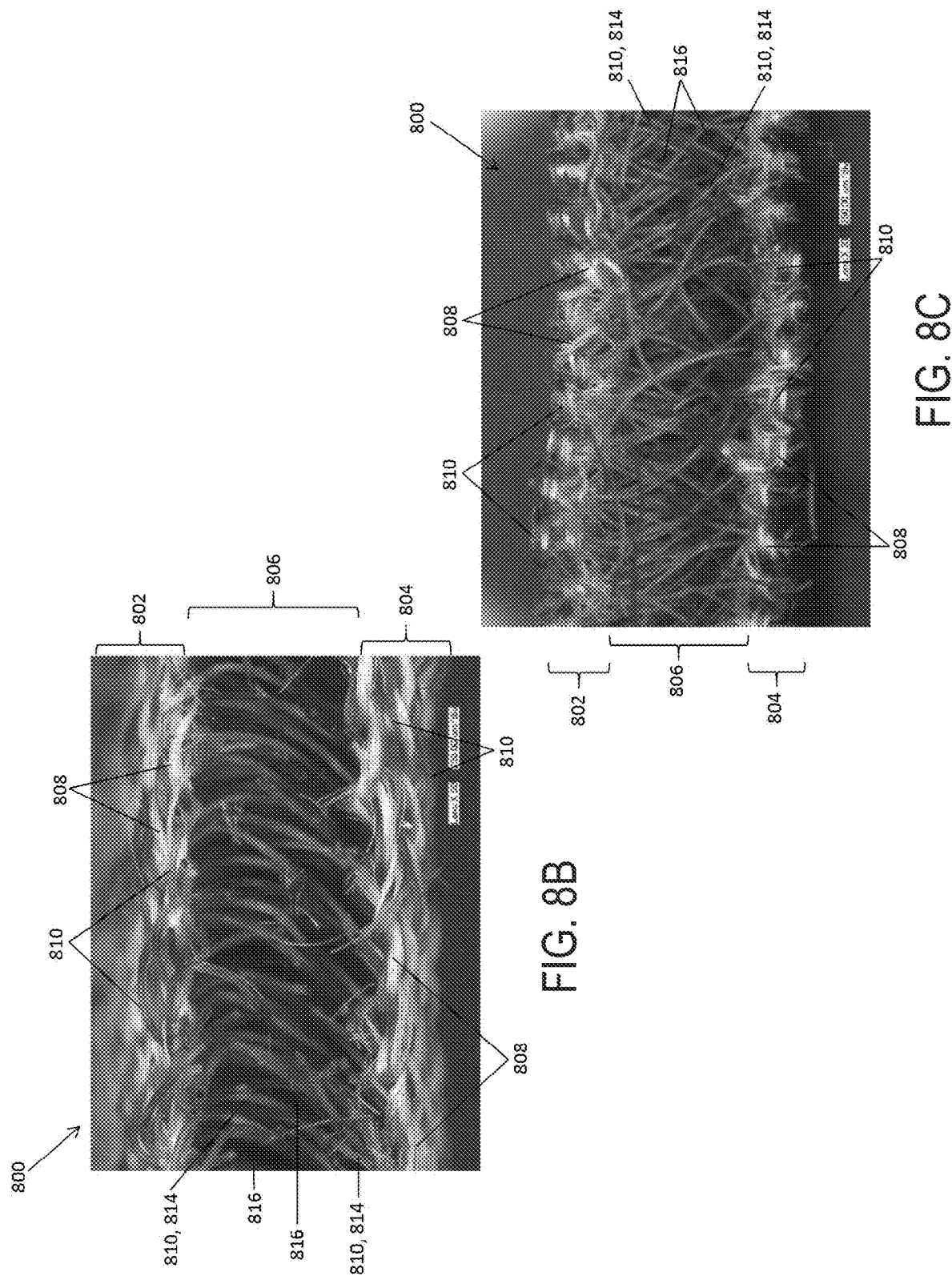

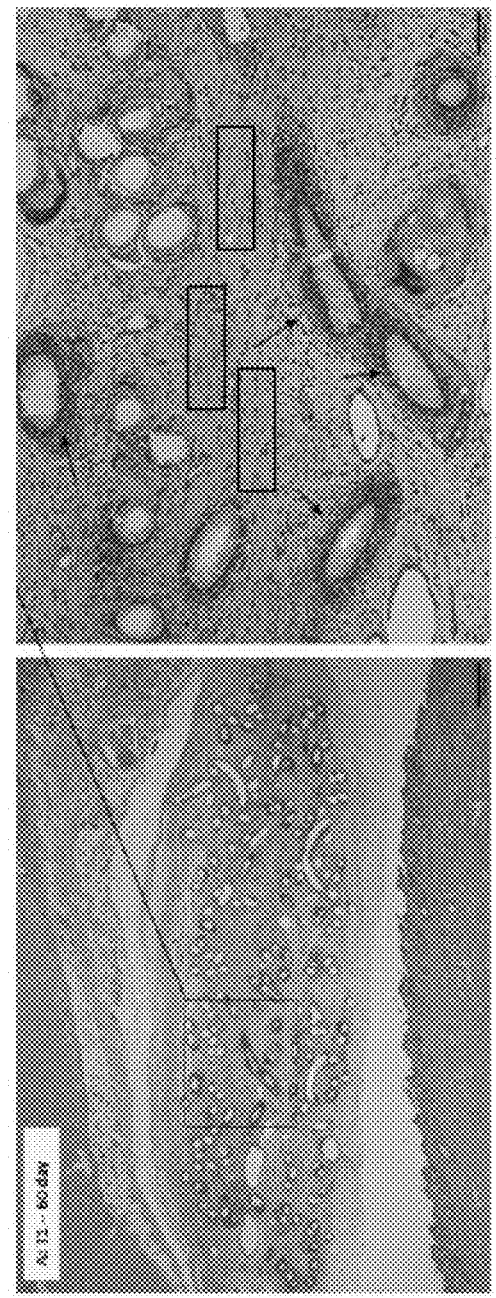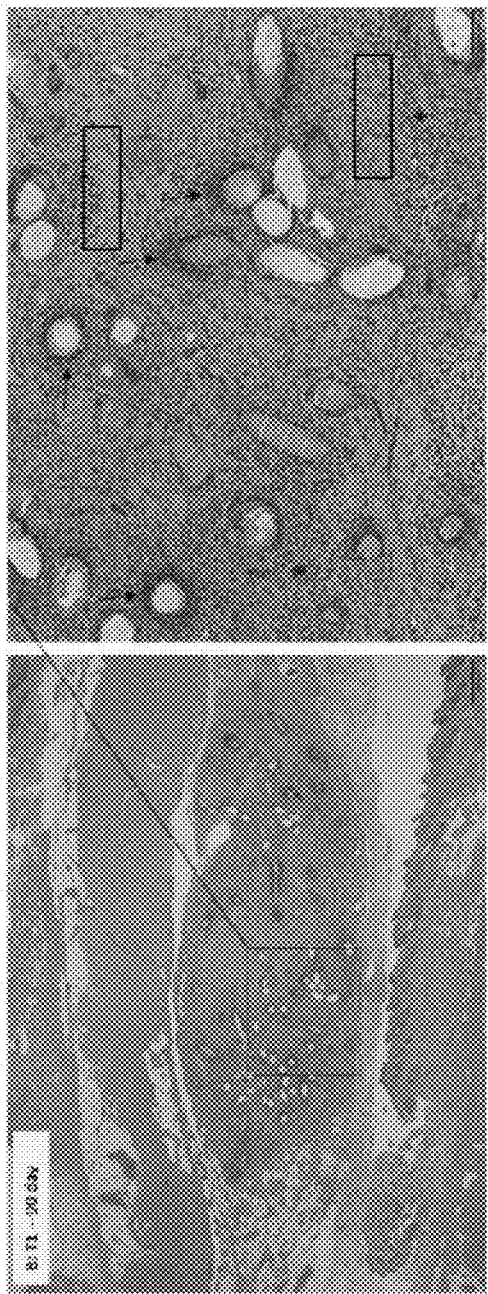
FIG. 10A  FIG. 10B  FIG. 11A  FIG. 11B

KNITTED TISSUE SCAFFOLDS

CROSS-REFERENCE TO RELATED APPLICATION

The present application is a continuation of U.S. patent application Ser. No. 17/208,280, filed on Mar. 22, 2021, and entitled "KNITTED TISSUE SCAFFOLDS," which is a continuation of U.S. patent application Ser. No. 15/901,103, now U.S. Pat. No. 10,982,360, filed on Feb. 21, 2018, and entitled "KNITTED TISSUE SCAFFOLDS," each of which is hereby incorporated by reference in its entirety.

FIELD

Knitted tissue scaffolds and methods for manufacturing the same are provided.

BACKGROUND

Surgical staplers are used in surgical procedures to close openings in tissue, blood vessels, ducts, shunts, or other objects or body parts involved in the particular procedure. The openings can be naturally occurring, such as passageways in blood vessels or an internal organ like the stomach, or they can be formed by the surgeon during a surgical procedure, such as by puncturing tissue or blood vessels to form a bypass or an anastomosis, or by cutting tissue during a stapling procedure.

Some surgical staplers require a surgeon to select the appropriate staples having the appropriate staple height for the tissue being stapled. For example, a surgeon could select tall staples for use with thick tissue and short staples for use with thin tissue. In some instances, however, the tissue being stapled does not have a consistent thickness and, thus, the staples cannot achieve the desired fired configuration at each staple site. As a result, a desirable seal at or near all of the stapled sites cannot be formed, thereby allowing blood, air, gastrointestinal fluids, and other fluids to seep through the unsealed sites.

Further, staples, as well as other objects and materials that can be implanted in conjunction with procedures like stapling, generally lack some characteristics of the tissue in which they are implanted. For example, staples and other objects and materials can lack the natural flexibility of the tissue in which they are implanted, and therefore are unable to withstand the varying intra-tissue pressures at the implantation site. This can lead to undesirable tissue tearing, and consequently leakage, at or near the staple site, and/or leakage between the apposed implant and tissue.

Accordingly, there remains a need for improved instruments and methods that address current issues with surgical staplers.

SUMMARY

Methods for manufacturing scaffolds and staple cartridge assemblies are provided.

In one exemplary embodiment, the method can include forming a first knitted layer that can include fibers of a first polymer and can be configured to mate with a cartridge deck, forming a second knitted layer that can include the first polymer fibers, and interknitting spacer fibers with the first and second knitted layers so as to connect the first and second knitted layers together in a spaced parallel relation. The spacer fibers can be formed of only a second polymer that is different than the first polymer in which the spacer fibers can be integrated with and extending between the first and second knitted layers. The first polymer fibers can have a diameter that is different than a diameter of the second polymer fibers. In one aspect, the method can also include annealing the first and second knitted layers interknitted with the spacer fibers.

In some aspects, the first polymer fibers can be multifilament fibers and the second polymer fibers can be monofilament fibers. In other aspects, the first polymer fibers can be configured to degrade at a first rate and the second polymer fibers can be configured to degrade at a second rate that is different than the first rate. In yet other aspects, the first polymer fibers can have a first glass transition temperature and the second polymer fibers can have a second glass transition temperature that is less than the first glass transition temperature.

In some aspects, the formation of the first knitted layer can include knitting the first polymer fibers according to a predetermined pattern. In other aspects, the formation of the second knitted layer can include knitting the first polymer fibers according to a predetermined pattern.

The first knitted layer can have a variety of configurations. For example, in one aspect, the first knitted layer can have openings that each have a size that is less than about ¼ of a width of a crown of a staple. In another aspect, the first knitted layer can further include fibers of a third polymer, and the formation of the first knitted layer can include knitting the first and third polymer fibers according to a predetermined pattern. In one embodiment, the third polymer fibers can be configured to degrade at a faster rate than a rate of degradation of the first polymer fibers. In another embodiment, the third polymer fibers can be configured to degrade at a faster than a rate of degradation of the second polymer fibers.

The second knitted layer can have a variety of configurations. For example, in one aspect, the second knitted layer can further include fibers of a third polymer in which the formation of the second knitted layer can include knitting the first and third polymer fibers according to a predetermined pattern.

In some aspects, the step of interknitting the spacer fibers with the first and second knitted layers can form a support layer therebetween. In such aspects, openings can be present in the first and second knitted layers and voids can be present in the support layer, with the voids being larger than the openings.

Methods for manufacturing staple cartridge assemblies are also provided. In one exemplary embodiment, the method can include heating a cartridge deck, and positioning a knitted elastically deformable, bioabsorbable scaffold against a surface of the cartridge deck, where the scaffold can include first and second knitted layers each having fibers of a first type and fibers of a second type in which the first type of fibers being predominantly present and the first type of fibers have a first glass transition temperature and the second type of fibers have a second glass transition temperature that is less than the first glass transition temperature, and a support layer disposed between the first and second knitted layers, the support layer being formed of the second type of fibers, where the cartridge deck is heated to a temperature of at least the second glass transition temperature. In one aspect, the first glass transition temperature is greater than the second glass transition temperature by at least about 30 degrees C.

In some aspects, the method can also include cooling the cartridge deck and scaffold applied thereto to a temperature that is less than the second glass transition temperature. In other aspects, the positioning of the scaffold against the surface of the cartridge deck can include placing the first knitted layer against the surface and applying force to the scaffold such that the first knitted layer bonds and conforms to a shape of the surface.

The cartridge deck can have a variety of configurations. For example, in one aspect, the cartridge deck can include a plurality of staples with each staple partially extending from the surface of the cartridge deck. In another aspect, the surface of the cartridge deck can include one or more attachment features that can be configured to enhance attachment of the scaffold to the cartridge deck.

Staple cartridge assemblies for use with a surgical stapling instrument and scaffolds for use with a surgical staple cartridge are also provided.

In one exemplary embodiment, a staple cartridge assembly is provided and can include a staple cartridge having a plurality of staples and a cartridge deck, and a knitted elastically deformable, bioabsorbable scaffold formed of at least two different fiber materials and having attachment properties such that the scaffold is configured to mate with the cartridge deck, where the staples are deployable through the scaffold into tissue captured against the scaffold. The scaffold can include first and second knitted layers and a support layer disposed between the first and second knitted layers. The first and second knitted layers can each include fibers of a first type and fibers of a second type, where the first type of fibers are predominantly present. The first type of fibers can have a first glass transition temperature and the second type of fibers can have a second glass transition temperature that is less than the first glass transition temperature. The support layer can be formed of the second type of fibers. In one aspect, the first glass transition temperature can be greater than the second glass transition temperature by at least about 30 degrees C. In another aspect, an outer surface of the cartridge deck can include one or more attachment features that are configured to engage the scaffold.

In some aspects, the second type of fibers can interconnect with the first type of fibers of the first and second knitted layers in a manner such that the first and second fibers are non-fixedly attached.

In some aspects, the first type of fibers can be multifilament fibers and the second type of fibers can be monofilament fibers. In one aspect, the first type of fibers can be coated with a bioabsorbable polymeric material.

The first and second type of fibers can be formed of a variety of materials. In one aspect, the first type of fibers can be formed of at least one of poly-L-lactic acid, a copolymer of glycolide and L-lactide, a copolymer of glycolic acid and lactic acid, poly(lactic-co-glycolic acid), poly(lactic acid), polyglycolide, and a copolymer of glycolide, caprolactone, trimethylene carbonate, and lactide. In another aspect, the second type of fibers can be formed of at least one of polydioxanone, a copolymer of polydioxanone and polyglycolide, a copolymer of lactide and polycaprolactone), a copolymer of glycolide, dioxanone, and trimethylene carbonate, poly(trimethylene carbonate), polyhydroxyalkanoate, and polyglyconate.

The scaffold can also have a variety of configurations. For example, in one aspect, the scaffold can be configured to be thermoformed to the cartridge deck, where the second knitted layer abuts the cartridge deck. In another aspect, the scaffold can be configured to apply a stress of at least about 3 gf/mm$^2$ to the captured tissue for at least 3 days when the scaffold is in a tissue deployed state. In yet another aspect, the scaffold can be configured to deform from an non-deformed height to a deformed height, where the non-deformed height is greater than a height of each staple of the plurality of staples when the staple is in a formed configuration.

In another exemplary embodiment, a staple cartridge assembly is provided and can include a staple cartridge having a plurality of staples and a cartridge deck, and a knitted elastically deformable, bioabsorbable scaffold, where the staples are deployable through the scaffold into tissue captured against the scaffold. The scaffold can include at least two layers. The first layer can be knitted and can include first and second fibers and the second layer includes only the second fibers. The first and second fibers can be formed of different materials and the first fibers can have a glass transition temperature that is greater than a glass transition temperature of the second fibers. The second fibers in the second layer can be knitted into the first knitted layer in a manner such that the second fibers form supporting members that are oriented substantially perpendicular to the first fibers in the first layer. In one aspect, the glass transition temperature of the first fibers can be greater than the glass transition temperature of the second fibers by at least about 30 degrees C. In another aspect, the first fibers can be coated with a bioabsorbable polymeric material.

In some aspects, the scaffold can also include a third layer that can include the first and second fibers, where the third layer can be knitted and the second layer can be positioned between the first and third layers.

In one aspect, the second fibers can interconnect with the first fibers in a manner such that the first and second fibers are non-fixedly attached.

The scaffold can also have a variety of configurations. For example, in one aspect, the scaffold can be configured to be thermoformed to the staple cartridge, where the second knitted layer abuts the cartridge deck. In another aspect, the scaffold can be configured to apply a stress of at least about 3 gf/mm$^2$ to the captured tissue for at least 3 days when the scaffold is in a tissue deployed state. In yet another aspect, the scaffold can be configured to deform from an undeformed height to a deformed height, where the undeformed height greater is than a height of each staple of the plurality of staples when the staple is in a formed configuration.

In some aspects, an outer surface of the cartridge deck can include one or more attachment features that are configured to engage the knitted scaffold.

In one exemplary embodiment, a scaffold is provided and can include first and second knitted layers each having fibers of a first type and fibers of a second type, where the first type of fibers being predominantly present, and a support layer disposed between the first and second knitted layers, where the support layer being formed of the second type of fibers. The first type of fibers can have a first glass transition temperature and the second type of fibers can have a second glass transition temperature that is less than the first glass transition temperature.

In one exemplary embodiment, a staple cartridge assembly is provided and can include staple cartridge having a plurality of staples and a cartridge deck, and a knitted bioabsorbable scaffold in which the staples are deployable through the scaffold into tissue captured against the scaffold. The scaffold can include a first knitted layer that can be configured to be positioned against tissue, a second knitted layer that can be configured to be positioned against the cartridge deck, and a support layer disposed between the first and second layers. The first knitted layer can have a plurality of openings formed therein and can be formed of fibers formed of a first bioabsorbable polymer. The second knitted layer can have a plurality of openings formed therein and can be formed of the fibers formed of the first bioabsorbable polymer, where the openings can have a size that is less than about ¼ of a width of a crown of the staples. The support layer can be formed of a fiber of a second bioabsorbable polymer. The fiber of the support layer can arranged to form standing fibers and a plurality of voids therebetween, where the standing fibers can be not fixedly attached to each other, and where a ratio of the voids to the second absorbable polymer within the support layer can be in the range of at least about 3:1. In one aspect, the scaffold can be configured to apply a stress of at least about 3 gf/mm$^2$ to the captured tissue for at least 3 days when the scaffold is in a tissue deployed state.

In one aspect, at least one of the first knitted layer and the second knitted layer can further include fibers formed of a third bioabsorbable polymer. In another aspect, the fibers of the support layer can be connected to the first and second knitted layers, such that the fibers are slidably interconnected with the fibers of the first and second knitted layers.

In some aspects, each opening of the plurality of openings in the first and second knitted layers can have a perimeter formed of the first and second bioabsorbable polymers. In another aspects, each opening of the plurality of openings formed in the second knitted layer can be configured to have a diameter from about 0.002 inches to 0.1 inches.

In one aspect, at least a portion of the voids in the support layer each can have a different size. In another aspect, the standing fibers can be oriented substantially perpendicular to the fibers of the first bioabsorbable polymer in the first and second knitted layers.

In another exemplary embodiment, a staple cartridge assembly is provided and can include a staple cartridge having a plurality of staples and a cartridge deck, and a knitted bioabsorbable scaffold in which the staples are deployable through the scaffold into tissue captured against the scaffold. The scaffold can include a first knitted layer that can be configured to be positioned against tissue, a second knitted layer that can be configured to be positioned against the cartridge deck, and a support layer. The first knitted layer can have a plurality of openings formed therein, and can be formed of multifilament fibers formed of a first bioabsorbable polymer and monofilament fibers formed of a second bioabsorbable polymer. The second knitted layer can have a plurality of openings formed therein and can be formed of the multifilament and monofilament fibers, where the openings can have a size that is less than about ¼ of a width of a crown of the staples. The support layer can have spacer fibers extending from the first knitted layer to the second knitted layer and a plurality of voids therebetween in which each spacer fiber can be formed of the monofilament fibers and ends of the spacer fibers can be slidably intertwined with the first and second knitted layers, where a ratio of the voids to the spacer fibers within the support layer can be in the range of at least about 3:1. In one aspect, the scaffold can be configured to apply a stress of at least about 3 gf/mm$^2$ to the captured tissue for at least 3 days when the scaffold is in a tissue deployed state.

In some aspects, each opening of the plurality of openings in the first and second knitted layers can have a perimeter formed of the multifilament and monofilament fibers. In other aspects, each opening of the plurality of openings formed in the second knitted layer can be configured to have a diameter from about 0.002 inches to 0.1 inches.

In one aspect, at least a portion of the voids in the support layer each have a different size. In another aspects, the spacer fibers can be oriented substantially perpendicular to the multifilament fibers of the first and second knitted layers.

In one exemplary embodiment, a scaffold is provided and can include a first knitted layer configured to be positioned against tissue, a second knitted layer configured to be positioned against a cartridge deck, and a support layer disposed between the first and second layers. The first knitted layer can have a plurality of openings formed therein and can be formed of fibers formed of a first bioabsorbable polymer. The second knitted layer can have a plurality of openings formed therein and can be formed of the fibers formed of the first bioabsorbable polymer, where the openings have a size that is less than about ¼ of a width of a crown of a staple within the cartridge deck. The support layer can be formed of a fiber of a second bioabsorbable polymer in which the fiber of the support layer is arranged to form standing fibers and a plurality of voids therebetween, where the standing fibers can be not fixedly attached to each other, and where a ratio of the voids to the second absorbable polymer within the support layer can be in the range of at least about 3:1.

In one exemplary embodiment, a staple cartridge assembly is provided and can include a staple cartridge having a plurality of staples and a cartridge deck, and a knitted elastically deformable, bioabsorbable scaffold attached to the cartridge deck and formed of at least three distinct zones, each having a different functionality, where the staples are deployable through the scaffold into tissue captured against the scaffold. The scaffold can include a first knitted zone that can be configured to promote tissue ingrowth, a second knitted zone that can be configured to be conformable so as to attach to the cartridge deck, and a spacer zone that is disposed between the first and second knitted zones and can be configured to support the first and second knitted zones, where openings are present in the first and second knitted zones and voids are present in the spacer zone, with the voids being larger than the openings. The first knitted zone can include first fibers made of a first bioabsorbable polymer and second fibers made of a second bioabsorbable polymer, where each first fiber has a fiber diameter that is less than a fiber diameter of each second fiber. The second knitted zone can include the first and second fibers of the first knitted zone. The spacer zone can be formed of the second fibers in which the second fibers are non-fixedly and slidably interconnected to the first fibers of the first and second knitted zones. In one aspect, the scaffold can be configured to apply a stress of at least about 3 gf/mm$^2$ to the captured tissue for at least 3 days when the scaffold is in a tissue deployed state.

In some aspects, the fiber diameters of the first fibers can be from about ⅕ to 1/20 of the fiber diameters of the second fibers. In other aspects, the fiber diameters of the first fibers can be about 1/10 of the fiber diameters of the second fibers.

In one aspect, the second fibers can extend from the first knitted zone to the second knitted zone such that the second fibers extend across the spacer zone and at least a portion of the second fibers within the spacer zone can be oriented substantially perpendicular to the first fibers of the first and second knitted zones.

The first and second type of fibers can be formed of a variety of materials. In one aspect, the first type of fibers can be formed of at least one of poly-L-lactic acid, a copolymer of glycolide and L-lactide, a copolymer of glycolic acid and lactic acid, poly(lactic-co-glycolic acid), poly(lactic acid), polyglycolide, and a copolymer of glycolide, caprolactone, trimethylene carbonate, and lactide. In another aspect, the second type of fibers can be formed of at least one of polydioxanone, a copolymer of polydioxanone and polyglycolide, a copolymer of lactide and polycaprolactone), a copolymer of glycolide, dioxanone, and trimethylene carbonate, poly(trimethylene carbonate), polyhydroxyalkanoate, and polyglyconate.

In another exemplary embodiment, a staple cartridge assembly is provided and can include a staple cartridge having a plurality of staples and a cartridge deck, and a knitted elastically deformable, bioabsorbable scaffold attached to the cartridge deck and formed of at least three distinct zones, each having a different functionality, where the staples are deployable through the scaffold into tissue captured against the scaffold. The scaffold can include a first zone that can have a knitted configuration and that can be configured to promote tissue ingrowth, where the first zone includes first fibers made of a first bioabsorbable polymer. The scaffold can also include a second zone that can be formed of second fibers made of a second bioabsorbable polymer and that can be configured to vertically support the first zone, where the second fibers are non-fixedly and slidably interconnected to the first fibers of the first zone such that the second fibers are substantially vertically oriented within the second zone. Each first fiber can have a fiber diameter that is less than a fiber diameter of each second fiber, and wherein openings are present in the first zone and voids are present in the second zone, with the voids being larger than the openings.

In some aspects, the scaffold can also include a third zone that can have a knitted configuration and that can be configured to be conformable so as to attach to the cartridge deck, where the third zone can include the first fibers and the second zone can be located between the first and third zones. In such instances, the second fibers can be non-fixedly and slidably interconnected to the first fibers of the third zone in which the second fibers can extend from the first zone to the third zone such that at least a portion of the second fibers are vertically oriented within the second zone. The scaffold can be configured to apply a stress of at least about 3 gf/mm$^2$ to the captured tissue for at least 3 days when the scaffold is in a tissue deployed state.

In some aspects, the fiber diameters of the first fibers can be from about 1/5 to 1/20 of the fiber diameters of the second fibers. In other aspects, the fiber diameters of the first fibers can be about 1/10 of the fiber diameters of the second fibers.

The first and second type of fibers can be formed of a variety of materials. In one aspect, the first type of fibers can be formed of at least one of poly-L-lactic acid, a copolymer of glycolide and L-lactide, a copolymer of glycolic acid and lactic acid, poly(lactic-co-glycolic acid), poly(lactic acid), polyglycolide, and a copolymer of glycolide, caprolactone, trimethylene carbonate, and lactide. In another aspect, the second type of fibers can be formed of at least one of polydioxanone, a copolymer of polydioxanone and polyglycolide, a copolymer of lactide and polycaprolactone), a copolymer of glycolide, dioxanone, and trimethylene carbonate, poly(trimethylene carbonate), polyhydroxyalkanoate, and polyglyconate.

In one exemplary embodiment, a scaffold is provided and can include a first knitted zone that is configured to promote tissue ingrowth, a second knitted zone that is configured to be conformable so as to attach to a cartridge deck, and a spacer zone that is disposed between the first and second knitted zones and is configured to support the first and second knitted zones, where openings are present in the first and second knitted zones and voids are present in the spacer zone, with the voids being larger than the openings. The first knitted zone can include first fibers made of a first bioabsorbable polymer and second fibers made of a second bioabsorbable polymer, where each first fiber has a fiber diameter that is less than a fiber diameter of each second fiber. The second knitted zone can include the first and second fibers of the first knitted zone. The spacer zone can be formed of the second fibers, where the second fibers can be non-fixedly and slidably interconnected to the first fibers of the first and second knitted zones.

In one exemplary embodiment, a staple cartridge assembly is provided can include a staple cartridge having a plurality of staples and a cartridge deck, and a knitted elastically deformable, bioabsorbable scaffold formed of at least two different fiber materials, where the staples are deployable through the scaffold into tissue captured against the scaffold and the scaffold is a multi-layered construct. The multi-layered construct can include a first layer that can have multifilament fibers, with at least a portion of the multifilament fibers being oriented in a direction that is substantially parallel to the cartridge deck, and a second layer that can be formed of monofilament fibers that are oriented in a direction that is substantially non-parallel to the cartridge deck in which the monofilament fibers can have a diameter that is less than an average diameter of the multifilament fibers. In one aspect, the monofilament fibers can be non-fixedly and slidably interconnected to the multifilament fibers of the first layer.

In some aspects, the multifilament fibers can be non-bonded multifilament fibers. In another aspect, the multifilament fibers can be not present within the second layer.

In some aspects, the multi-layered construct can also include a third layer that can have the multifilament fibers, with at least a portion of the multifilament fibers being oriented in a direction that is substantially parallel to the cartridge deck. The second layer can be positioned between the first and third layers. In one aspect, the monofilament fibers can be non-fixedly and slidably interconnected to the first fibers of the first layer and third layers. In another aspect, the scaffold can be configured to apply a stress of at least about 3 gf/mm$^2$ to the captured tissue for at least 3 days when the scaffold is in a tissue deployed state.

The multifilament and monofilament fibers can be formed of a variety of materials. In one aspect, the multifilament fibers can be formed of at least one of poly-L-lactic acid, a copolymer of glycolide and L-lactide, a copolymer of glycolic acid and lactic acid, poly(lactic-co-glycolic acid), poly(lactic acid), polyglycolide, and a copolymer of glycolide, caprolactone, trimethylene carbonate, and lactide. In another aspect, the monofilament fibers can be formed of at least one of polydioxanone, a copolymer of polydioxanone and polyglycolide, a copolymer of Lactide and polycaprolactone), a copolymer of glycolide, dioxanone, and trimethylene carbonate, poly(trimethylene carbonate), polyhydroxyalkanoate, and polyglyconate.

In another exemplary embodiment, a surgical cartridge assembly is provided and can include a staple cartridge having a plurality of staples and a cartridge deck, and a knitted elastically deformable, bioabsorbable scaffold formed of at least two different fiber materials, where the staples are deployable through the scaffold into tissue captured against the scaffold and the scaffold is a multi-layered construct. The multi-layered construct can include first and second layers each having multifilament fibers, with at least a portion of the multifilament fibers being oriented in a direction that is substantially parallel to the cartridge deck, and an intermediate layer positioned between the first and second layers and can be formed of only monofilament fibers that are oriented in a direction that is substantially non-parallel to the cartridge deck. The monofilament fibers can have a diameter that is less than an average diameter of the multifilament fibers. In one aspect, the monofilament fibers can be non-fixedly and slidably interconnected to the multifilament fibers of the first and second layers. In another aspect, each of the multifilament fibers can be non-bonded multifilament fibers.

In some aspects, the scaffold can be configured apply a stress of at least about 3 gf/mm$^2$ to the captured tissue for at least 3 days when the scaffold is in a tissue deployed state.

The multifilament and monofilament fibers can be formed of a variety of materials. In one aspect, the multifilament fibers can be formed of at least one of poly-L-lactic acid, a copolymer of glycolide and L-lactide, a copolymer of glycolic acid and lactic acid, poly(lactic-co-glycolic acid), poly(lactic acid), polyglycolide, and a copolymer of glycolide, caprolactone, trimethylene carbonate, and lactide. In another aspect, the monofilament fibers can be formed of at least one of polydioxanone, a copolymer of polydioxanone and polyglycolide, a copolymer of Lactide and polycaprolactone), a copolymer of glycolide, dioxanone, and trimethylene carbonate, poly(trimethylene carbonate), polyhydroxyalkanoate, and polyglyconate.

In one exemplary embodiment, a scaffold is provided and can include a first layer that can be configured to mate to a cartridge deck, and a second layer. The first layer can have multifilament fibers, with at least a portion of the multifilament fibers configured to be oriented in a direction that is substantially parallel to the cartridge deck. The second layer can be formed of monofilament fibers that are configured to be oriented in a direction that is substantially non-parallel to the cartridge deck. The monofilament fibers can have a diameter that is less than an average diameter of the multifilament fibers.

In some aspects, the scaffold can also include a third layer that can have the multifilament fibers, with at least a portion of the multifilament fibers configured to be oriented in a direction that is substantially parallel to the cartridge deck. The second layer can be positioned between the first and third layers.

In one exemplary embodiment, a staple cartridge assembly is provided and can include a staple cartridge having a plurality of staples and a cartridge deck, a knitted elastically deformable, bioabsorbable composite scaffold formed of a plurality of fiber materials, where the scaffold is configured to mate with the cartridge deck and the staples are deployable through the scaffold into tissue captured against the scaffold. The scaffold can include a tissue interaction surface and a cartridge deck interaction surface, and an intermediate layer that can be disposed between the tissue interaction surface and the cartridge deck interaction surface. The tissue interaction surface and the cartridge deck interaction surface can each be on opposite sides of the scaffold and each can have fibers of a first polymer and fibers of a second polymer, where the first polymer fibers can be multifilament fibers. The first polymer fibers can form a structural component of the tissue interaction surface and the cartridge deck interaction surface with a variable stiffness profile over time following implantation. The second polymer fibers can degrade at a rate greater than that of the first polymer fibers without substantially affecting the stiffness profile of the structural component. The intermediate layer can be formed of monofilament fibers that are oriented in a direction that is substantially non-parallel to the cartridge deck. In one aspect, the multifilament fibers can have average diameter that is greater than a diameter of the monofilament fibers. In another aspect, the scaffold can be configured to apply a stress of at least about 3 gf/mm$^2$ to the captured tissue for at least 3 days when the scaffold is in a tissue deployed state.

In some aspects, the multifilament fibers can each include the second polymer fibers at a range of about 15% to 85%. In other aspects, the multifilament fibers can each include the second polymer fibers at a range of about 25% to 45%.

In some aspects, the second polymer fibers can have a fiber diameter from about 0.005 mm to 0.02 mm. In one aspect, the second polymer fibers can be formed of a copolymer of glycolide and L-lactide.

In some aspects, the multifilament fibers can include about 6 to 40 filaments. In one aspect, the filaments are formed of the first polymer fibers. In another aspect, at least one filament is formed of the first polymer fiber and at least one filament is formed of the second polymer fiber.

In some aspects, the first polymer fibers can be formed of at least one of poly-L-lactic acid, a copolymer of glycolide and L-lactide, a copolymer of glycolic acid and lactic acid, poly(lactic-co-glycolic acid), poly(lactic acid), polyglycolide, and a copolymer of glycolide, caprolactone, trimethylene carbonate, and lactide.

In some aspects, the monofilament fibers can be formed of at least one of polydioxanone, a copolymer of polydioxanone and polyglycolide, a copolymer of lactide and polycaprolactone), a copolymer of glycolide, dioxanone, and trimethylene carbonate, poly(trimethylene carbonate), polyhydroxyalkanoate, and polyglyconate.

In one exemplary embodiment, a scaffold is provided and can include a tissue interaction surface and a cartridge deck interaction surface, and an intermediate layer disposed between the tissue interaction surface and the cartridge deck interaction surface. The tissue interaction surface and a cartridge deck interaction surface can each be on opposite sides of the scaffold and each can have fibers of a first polymer and fibers of a second polymer, where the first polymer fibers can be multifilament fibers. The first polymer fibers can form a structural component of the tissue interaction surface and the cartridge deck interaction surface with a variable stiffness profile over time following implantation. The second polymer fibers can degrade at a rate greater than that of the first polymer fibers without substantially affecting the stiffness profile of the structural component. The intermediate layer being can formed of monofilament fibers that are oriented in a direction that is substantially non-parallel to the cartridge deck. In another aspect, the scaffold can be configured to apply a stress of at least about 3 gf/mm$^2$ to the captured tissue for at least 3 days when the scaffold is in a tissue deployed state.

In some aspects, the multifilament fibers can have an average diameter that is greater than a diameter of the monofilament fibers. In other aspects, the multifilament fibers can each include the second polymer fibers at a range of about 15% to 85%.

In some aspects, the second polymer fibers can have a fiber diameter from about 0.005 mm to 0.02 mm. In one aspect, the second polymer fibers can be formed of a copolymer of glycolide and L-lactide.

In some aspects, the multifilament fibers can include about 6 to 40 filaments. In one aspect, at least one filament is formed of the first polymer fiber and at least one filament is formed of the second polymer fiber.

In some aspects, the first polymer fibers can be formed of at least one of poly-L-lactic acid, a copolymer of glycolide and L-lactide, a copolymer of glycolic acid and lactic acid, poly(lactic-co-glycolic acid), poly(lactic acid), polyglycolide, and a copolymer of glycolide, caprolactone, trimethylene carbonate, and lactide.

In some aspects, the monofilament fibers can be formed of at least one of polydioxanone, a copolymer of polydioxanone and polyglycolide, a copolymer of lactide and polycaprolactone), a copolymer of glycolide, dioxanone, and trimethylene carbonate, poly(trimethylene carbonate), polyhydroxyalkanoate, and polyglyconate.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

This invention will be more fully understood from the following detailed description taken in conjunction with the accompanying drawings, in which:

FIG. 8B is a magnified cross-sectional view of the scaffold of FIG. 8A taken at B-B;

FIG. 8C is another magnified cross-sectional view of the scaffold of FIG. 8A taken at C-C;

FIG. 10A is a histopathology image of an implanted scaffold removed at 60 days as discussed in Example 2.

FIG. 10B is a magnified view of section 10B in FIG. 10A;

FIG. 11A is a histopathology image of an implanted scaffold removed at 90 days as discussed in Example 2;

FIG. 11B is a magnified view of section 11B in FIG. 11A;

DETAILED DESCRIPTION

Figure 1:
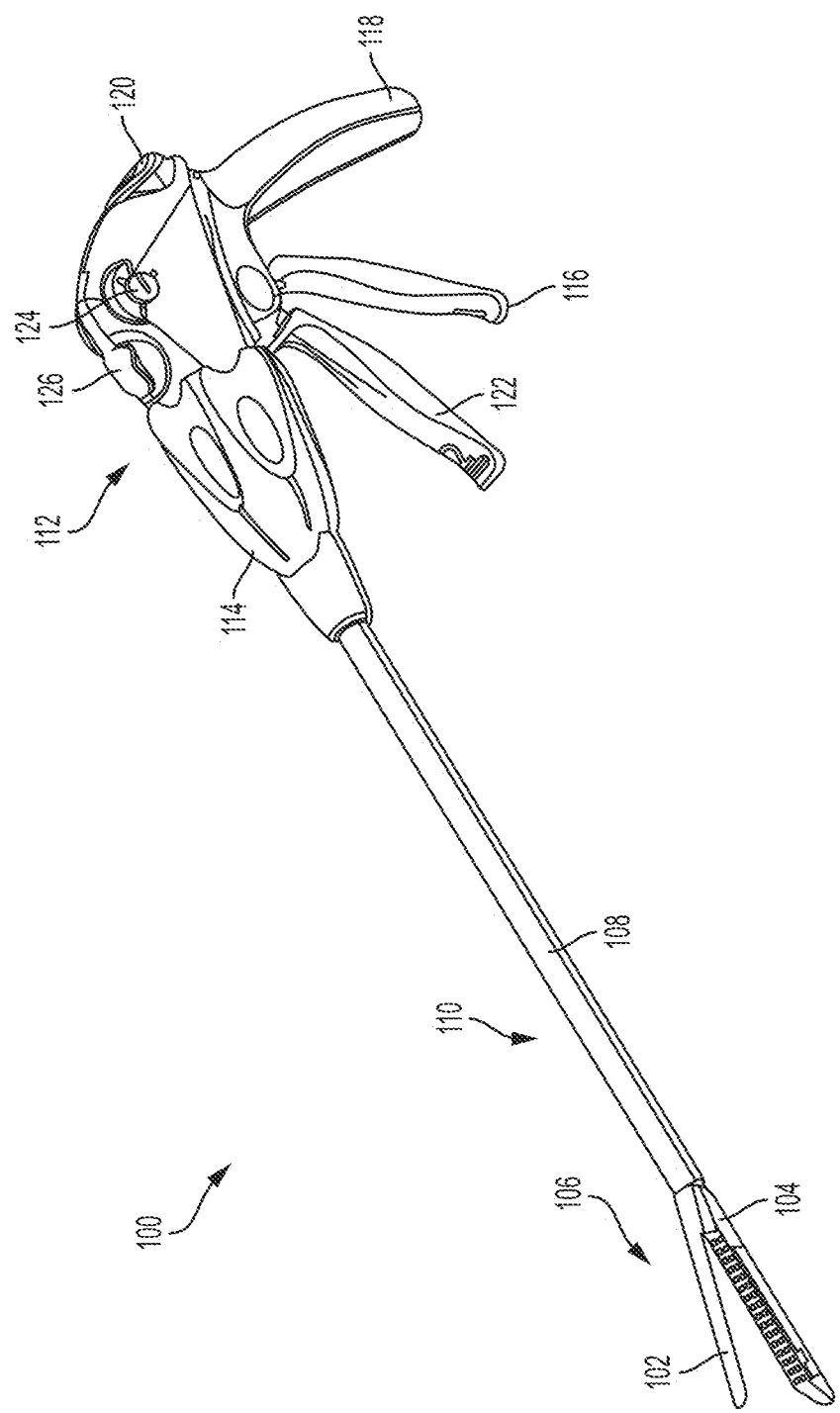
FIG. 1 is a perspective view of one exemplary embodiment of a conventional surgical stapling and severing instrument.

Certain exemplary embodiments will now be described to provide an overall understanding of the principles of the structure, function, manufacture, and use of the instruments and methods disclosed herein. One or more examples of these embodiments are illustrated in the accompanying drawings. Those skilled in the art will understand that the instruments, systems, and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Further, in the present disclosure, like-named components of the embodiments generally have similar features, and thus within a particular embodiment each feature of each like-named component is not necessarily fully elaborated upon. Additionally, to the extent that linear or circular dimensions are used in the description of the disclosed systems, instruments, and methods, such dimensions are not intended to limit the types of shapes that can be used in conjunction with such systems, instruments, and methods. A person skilled in the art will recognize that an equivalent to such linear and circular dimensions can easily be determined for any geometric shape. Sizes and shapes of the systems and instruments, and the components thereof, can depend at least on the anatomy of the subject in which the systems and instruments will be used, the size and shape of components with which the systems and instruments will be used, and the methods and procedures in which the systems and instruments will be used.

It will be appreciated that the terms "proximal" and "distal" are used herein with reference to a user, such as a clinician, gripping a handle of an instrument. Other spatial terms such as "front" and "rear" similarly correspond respectively to distal and proximal. It will be further appreciated that for convenience and clarity, spatial terms such as "vertical" and "horizontal" are used herein with respect to the drawings. However, surgical instruments are used in many orientations and positions, and these spatial terms are not intended to be limiting and absolute.

Values or ranges may be expressed herein as "about" and/or from/of "about" one particular value to another particular value. When such values or ranges are expressed, other embodiments disclosed include the specific value recited and/or from/of the one particular value to another particular value. Similarly, when values are expressed as approximations, by the use of antecedent "about," it will be understood that here are a number of values disclosed therein, and that the particular value forms another embodiment. It will be further understood that there are a number of values disclosed therein, and that each value is also herein disclosed as "about" that particular value in addition to the value itself. In embodiments, "about" can be used to mean, for example, within 10% of the recited value, within 5% of the recited value or within 2% of the recited value.

For purposes of describing and defining the present teachings, it is noted that unless indicated otherwise, the term "substantially" is utilized herein to represent the inherent degree of uncertainty that may be attributed to any quantitative comparison, value, measurement, or other representation. The term "substantially" is also utilized herein to represent the degree by which a quantitative representation may vary from a stated reference without resulting in a change in the basic function of the subject matter at issue.

Surgical staple cartridge assemblies and methods for manufacturing the same are provided. In general, a staple cartridge assembly is provided having a staple cartridge that includes a cartridge deck with a plurality of staples disposed therein. The staple cartridge assembly also includes a knitted elastically deformable, bioabsorbable scaffold that is configured to releasably mate with the cartridge deck and allow the staples to be deployed therethrough into tissue. The scaffold can be releasably mated to the cartridge deck such that when a staple is deployed from the cartridge deck and into tissue, at least a portion of the scaffold can attach to the tissue captured by the staple. As discussed herein, the scaffold can be configured to compensate for variations in tissue properties, such as variations in the tissue thickness, and/or promote tissue ingrowth when the scaffold is stapled to tissue. For example, the scaffold can be configured to apply a stress of at least about 3 gf/mm$^2$ to tissue for at least 3 days when in a tissue deployed state (e.g., when the scaffold is stapled to tissue in vivo). An exemplary staple cartridge assembly can include a variety of features to facilitate application of a surgical staple, as described herein and illustrated in the drawings. However, a person skilled in the art will appreciate that the staple cartridge assembly can include only some of these features and/or it can include a variety of other features known in the art. The staple cartridge assemblies described herein are merely intended to represent certain exemplary embodiments. Moreover, while the scaffolds are described in connection with surgical staple cartridge assemblies, the scaffolds can be used in connection with any type of surgical instrument.

FIG. 1 illustrates an exemplary surgical stapling and severing instrument 100 suitable for use with an implantable adjunct such as, for example, a scaffold. The surgical stapling and severing instrument 100 can include an anvil 102 which may be repeatedly opened and closed about its pivotal attachment to an elongate staple channel 104. A staple applying assembly 106 may comprise the anvil 102 and the channel 104, wherein the assembly 106 can be proximally attached to an elongate shaft 108 forming an implement portion 110. When the staple applying assembly 106 is closed, or at least substantially closed, the implement portion 110 can present a sufficiently small cross-section suitable for inserting the staple applying assembly 106 through a trocar. While the instrument 100 is configured to staple and sever tissue, surgical instruments configured to staple but not sever tissue is also contemplated herein.

In various instances, the staple applying assembly 106 is manipulated by a handle 112 connected to the elongate shaft 108. The handle 112 can include user controls such as a rotation knob 114 that rotates the elongate shaft 108 and the staple applying assembly 106 about a longitudinal axis of the elongate shaft 108 and a closure trigger 116, which can pivot in front of a pistol grip 118 to close the staple applying assembly 106. A closure release button 120 is outwardly presented on the handle 112 when the closure trigger 116 is clamped such that the closure release button 120 can be depressed to unclamp the closure trigger 116 and open the staple applying assembly 106, for example.

A firing trigger 122, which can pivot in front of the closure trigger 116, causes the staple applying assembly 106 to simultaneously sever and staple tissue clamped therein. In various instances, multiple firing strokes can be employed using the firing trigger 122 to reduce the amount of force required to be applied by the surgeon's hand per stroke. In certain embodiments, the handle 112 can comprise one or more rotatable indicator wheels such as, for example, rotatable indicator wheel 124 which can indicate the firing progress. A manual firing release lever 126 can allow the firing system to be retracted before full firing travel has been completed, if desired, and, in addition, the firing release lever 126 can allow a surgeon, or other clinician, to retract the firing system in the event that the firing system binds and/or fails.

Additional details on the surgical stapling and severing instrument 100 and other surgical stapling and severing instruments suitable for use with the present disclosure are described, for example, in U.S. Pat. No. 9,332,984 and in U.S. Patent Application Publication No. 2009/0090763, the disclosures of which are incorporated herein by reference in their entirety. Further, the surgical stapling and severing instrument need not include a handle, but instead a housing that is configured to couple to a surgical robot, for example, as described in U.S. patent application Ser. No. 15/689,198, filed on Aug. 29, 2017 to Frederick E. Shelton et al., the disclosure of which is incorporated herein by reference in its entirety.

Figure 3:
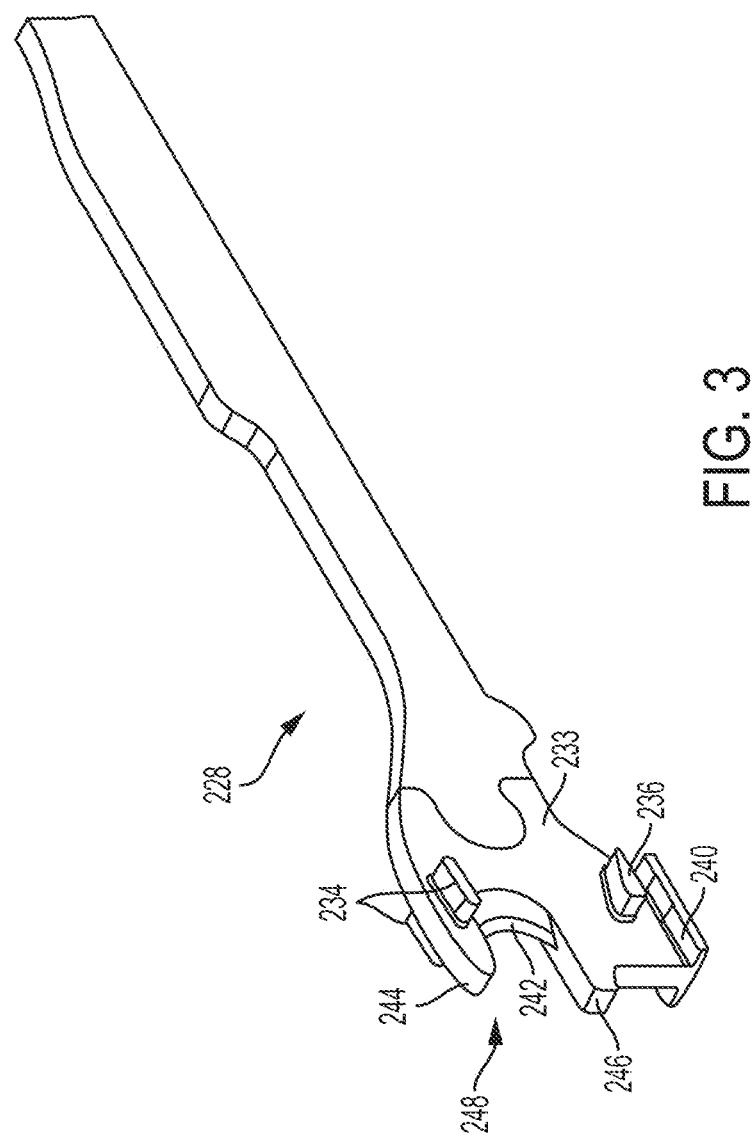
FIG. 3 is a perspective view of a knife and firing bar ("E-beam") of the surgical stapling and severing instrument of FIG. 1.
Figure 2:
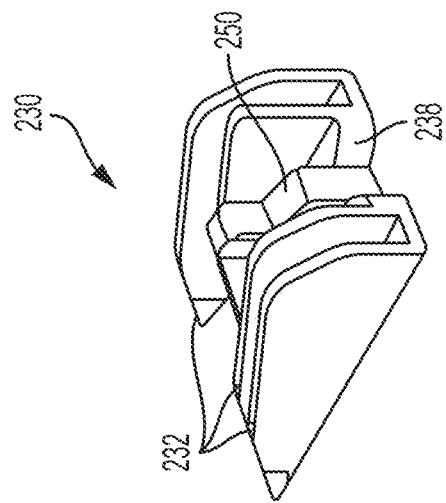
FIG. 2 is a perspective view of a wedge sled of a staple cartridge of the surgical stapling and severing instrument of FIG. 1.

With reference to FIGS. 2 and 3, a firing assembly such as, for example, firing assembly 228 can be utilized with a surgical stapling and severing instrument, such as instrument 100 in FIG. 1, to advance a wedge sled 230 which comprises a plurality of wedges 232 configured to deploy staples from a staple applying assembly, like staple applying assembly 106 in FIG. 1 into tissue captured between an anvil, like anvil 102 in FIG. 1 and an elongate staple channel, like channel 104 in FIG. 1. Furthermore, an E-beam 233 at a distal portion of the firing assembly 228 may fire the staples from the staple applying assembly as well as position the anvil relative to the elongate staple channel during firing. The E-beam 233 includes a pair of top pins 234, a pair of middle pins 236 which may follow portion 238 of the wedge sled 230, and a bottom pin or foot 240, as well as a sharp cutting edge 242, which can be configured to sever the captured tissue as the firing assembly 228 is advanced distally. In addition, integrally formed and proximally projecting top guide 244 and middle guide 246 bracketing each vertical end of the cutting edge 242 may further define a tissue staging area 248 assisting in guiding tissue to the sharp cutting edge 242 prior to being severed. The middle guide 246 may also serve to engage and fire the staple applying assembly by abutting a stepped central member 250 of the wedge sled 230 that effects staple formation by the staple applying assembly.

Figure 4:
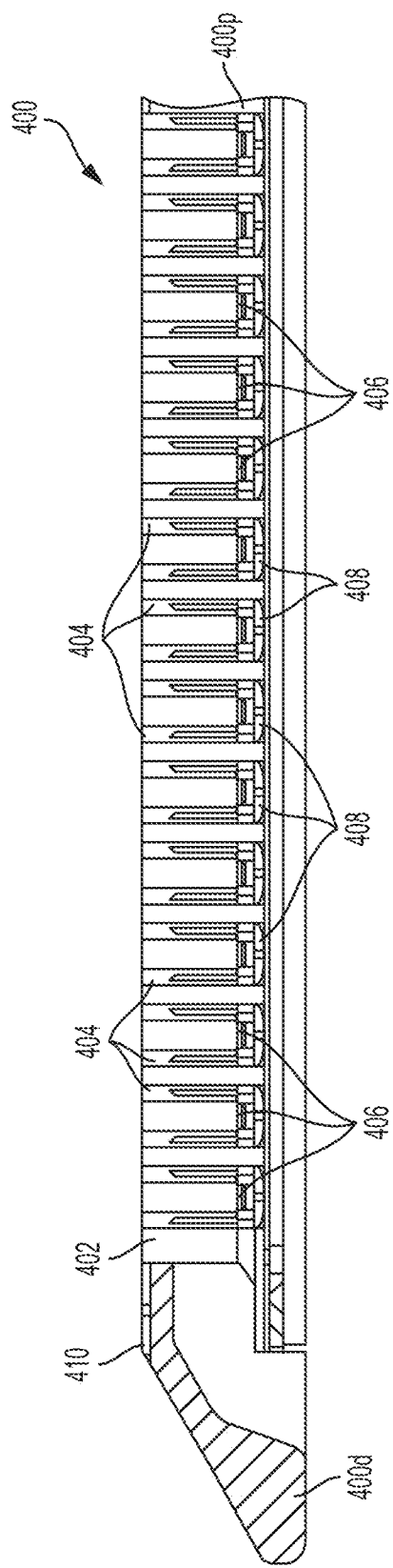
FIG. 4 is a longitudinal cross-sectional view of a surgical cartridge that can be disposed within the stapling and severing instrument of FIG. 1.

Referring to FIG. 4, a staple cartridge 400 can be utilized with a surgical stapling and severing instrument, like surgical stapling and severing instrument 100 in FIG. 1, and can include a cartridge deck 402 and a plurality of staple cavities 404. A staple 406, for example, can be removably positioned in each staple cavity 404. The staple 406 in a unfired (pre-deployed) configuration is shown in more detail in FIG. 5. The staple cartridge 400 can also include a longitudinal channel that can be configured to receive a firing and/or cutting member, e.g., an E-beam, like E-beam 233 in FIG. 3.

Figure 5:
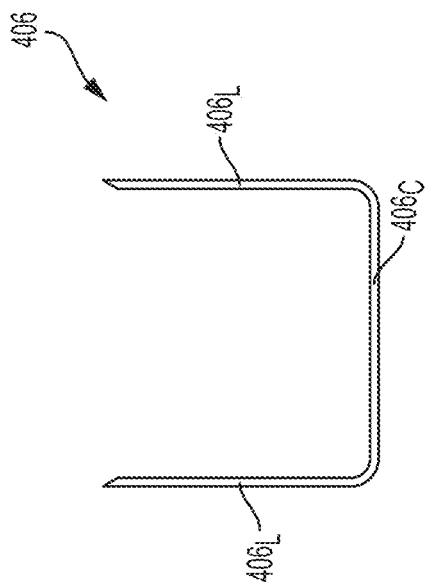
FIG. 5 is a top view of a staple in an unfired (pre-deployed) configuration that can be disposed within the staple cartridge of the surgical cartridge assembly of FIG. 4.

Each staple 406 can comprise a crown (base) 406c and one or more legs 406$_L$ extending from the crown 406. Prior to the staples 406 being deployed, the crowns 406c of the staples 406 can be supported by staple drivers 408 positioned within the staple cartridge 400 and, concurrently, the legs 406$_L$ of the staples 406 can be at least partially contained within the staple cavities 404. Further, the staple legs 406$_L$ of the staples 406 can extend beyond the tissue-contacting surface 410 of the staple cartridge 400 when the staples 406 are in their unfired positions. In certain instances, as shown in FIG. 5, the tips of the staple legs 406$_L$ can comprise sharp tips which can incise and penetrate tissue.

The staples 406 can be deployed between an unfired position and a fired position such that the legs 406$_L$ move through the staple cavities 404, penetrate tissue positioned between an anvil, like anvil 102 in FIG. 1, and the staple cartridge 400, and contact the anvil. As the legs $406_L$ are deformed against the anvil, the legs $406_L$ of each staple 406 can capture a portion of the tissue within each staple 406 and apply a compressive force to the tissue. Further, the legs $406_L$ of each staple 406 can be deformed downwardly toward the crown 406c of the staple 406 to form a staple entrapment area in which the tissue can be captured therein. In various instances, the staple entrapment area can be defined between the inner surfaces of the deformed legs and the inner surface of the crown of the staple. The size of the entrapment area for a staple can depend on several factors such as the length of the legs, the diameter of the legs, the width of the crown, and/or the extent in which the legs are deformed, for example.

In use, an anvil, like anvil 102 in FIG. 1, can be moved into a closed position by depressing a closure trigger, like closure trigger 116 in FIG. 1, to advance an E-beam, like E-beam 233 in FIG. 3. The anvil can position tissue against a tissue-contacting surface 410 of the staple cartridge 400. Once the anvil has been suitably positioned, the staples 406 can be deployed.

To deploy staples 406, as discussed above, a staple-firing sled, like sled 230 in FIG. 2, can be moved from a proximal end 400p toward a distal end 400d of the staple cartridge 400. As a firing assembly, like firing assembly 228 in FIG. 3, is advanced, the sled can contact the staple drivers 408 and lift the staple drivers 408 upwardly within the staple cavities 404. In at least one example, the sled and the staple drivers 408 can each include one or more ramps, or inclined surfaces, which can co-operate to move the staple drivers 408 upwardly from their unfired positions. As the staple drivers 408 are lifted upwardly within their respective staple cavities 404, the staple drivers 408 can lift the staples 406 upwardly such that the staples 406 can emerge from their staple cavities 404 and penetrate into tissue. In various instances, the sled can move several staples upwardly at the same time as part of a firing sequence.

A person skilled in the art will appreciate that, while scaffolds are shown and described below, the scaffolds disclosed herein can be used with other surgical instruments, and need not be coupled to a staple cartridge as described.

As discussed above, with some surgical staplers, a surgeon is often required to select the appropriate staple having the appropriate staple height for the tissue that is to be stapled. For example, a surgeon could select tall staples for use with thick tissue and short staples for use with thin tissue. In some instances, however, the tissue being stapled does not have a consistent thickness and, thus, the staples cannot achieve the desired fired configuration for every section of the stapled tissue (e.g., thick and thin tissue sections). The inconsistent thickness of tissue can also lead to undesirable leakage and/or tearing of tissue at the staple site when staples with the same or substantially height are used, particularly when the staple site is exposed to intra-tissue pressures at the staple site and/or along the staple line.

Accordingly, various embodiments of scaffolds are provided that can be configured to compensate for varying thickness of tissue that is captured within fired (deployed) staples to avoid the need to take into account staple height when stapling tissue during surgery. That is, the scaffolds described herein can allow a set of staples with the same or similar heights to be used in stapling tissue of varying thickness (i.e., from thin to thick tissue) while also, in combination with the scaffold, provide adequate tissue compression within and between fired staples. Thus, the scaffolds described herein can maintain suitable compression against thin or thick tissue stapled thereto to thereby minimize leakage and/or tearing of tissue at the staple sites.

Alternatively or in addition, the scaffold can be configured to promote tissue ingrowth. In various instances, it is desirable to promote the ingrowth of tissue into an implantable scaffold, to promote the healing of the treated tissue (e.g. stapled and/or incised tissue) and/or to accelerate the patient's recovery. More specifically, the ingrowth of tissue into an implantable scaffold may reduce the incidence, extent, and/or duration of inflammation at the surgical site. Tissue ingrowth into and/or around the implantable scaffold may manage the spread of infections at the surgical site, for example. The ingrowth of blood vessels, especially white blood cells, for example, into and/or around the implantable scaffold may fight infections in and/or around the implantable scaffold and the adjacent tissue. Tissue ingrowth may also encourage the acceptance of foreign matter (e.g., the implantable scaffold and the staples) by the patient's body and may reduce the likelihood of the patient's body rejecting the foreign matter. Rejection of foreign matter may cause infection and/or inflammation at the surgical site.

In general, the scaffolds provided herein are designed and positioned atop a staple cartridge, like staple cartridge 400 in FIG. 4, such that when the staples are fired (deployed) from the cartridge deck of the staple cartridge, the staples penetrate through the scaffold and into tissue. As the legs of the staple are deformed against the anvil that is positioned opposite the staple cartridge assembly, the deformed legs capture a portion of the scaffold and a portion of the tissue within each staple. That is, when the staple is fired into tissue, at least a portion of the scaffold becomes positioned between the tissue and the fired staple. While the scaffolds described herein are configured to be attached to a staple cartridge of a staple cartridge assembly, it is also contemplated herein that the scaffolds can be configured to mate with other instrument components, such as a jaw of a surgical stapler.

Figure 6:
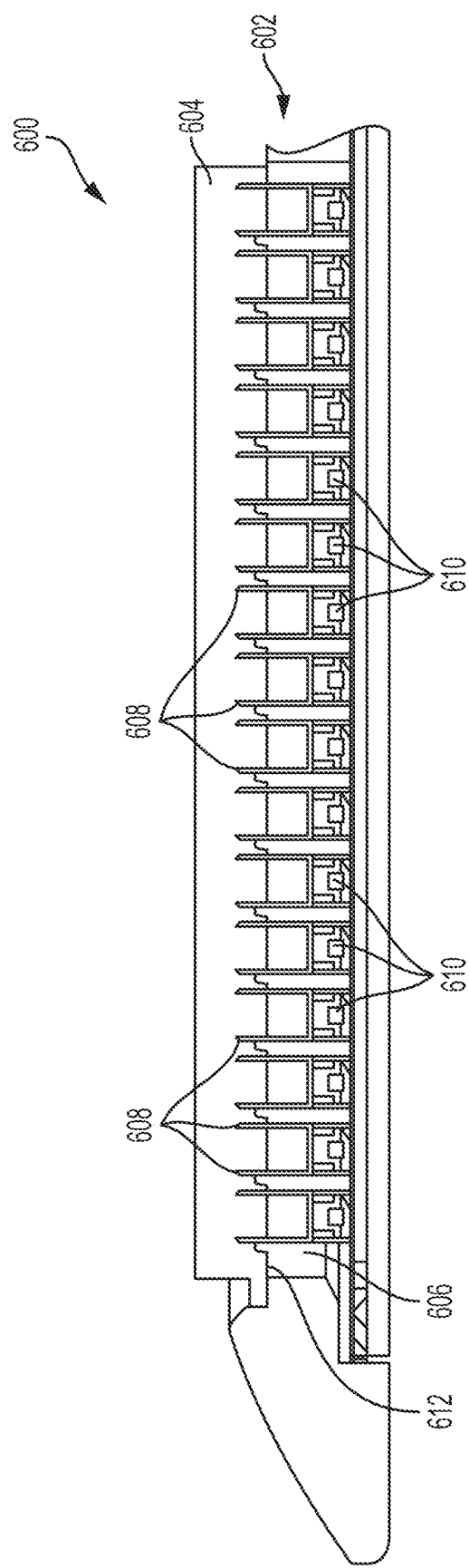
FIG. 6 is a longitudinal cross-sectional view of an exemplary embodiment of a surgical cartridge assembly having a scaffold attached to a cartridge deck.

FIG. 6 illustrates an exemplary embodiment of a staple cartridge assembly 600 that includes a staple cartridge 602 and a scaffold 604. Aside from the differences described in detail below, the staple cartridge 602 can be similar to staple cartridge 400 (FIG. 4) and is therefore not described in detail herein. As shown, the scaffold 604 is positioned against the staple cartridge 602. The staple cartridge can include a cartridge deck 606 and a plurality of staples 608, like staples 406 shown in FIGS. 4 and 5. The staples 608 can be any suitable unformed (pre-deployed) height. For example, the staples 608 can have an unformed height between about 2 mm to 4.8 mm. Prior to deployment, the crowns of the staples 608 can be supported by staple drivers 610.

In the illustrated embodiment, the scaffold 604 can be mated to an outer surface 612, for example a tissue-contacting, surface, of the cartridge deck 606. The outer surface 612 of the cartridge deck 606 can include one or more attachment features. The one or more attachments features can be configured to engage the scaffold 604 to avoid undesirable movements of the scaffold 604 relative to the cartridge deck 606 and/or premature release of the scaffold 604 from the cartridge deck 606, Exemplary attachment features can be found in U.S. Patent Publication No. 2016/0106427, which is incorporated by reference herein in its entirety.

The scaffold 604 is elastically deformable to permit the scaffold to compress to varying heights to thereby compensate for different tissue thickness that are captured within a deployed staple. The scaffold 604 has an uncompressed (undeformed), or pre-deployed, height and is configured to deform to one of a plurality of compressed (deformed), or deployed, heights. For example, the scaffold 604 can have an uncompressed height which is greater than the fired height of the staples 608 (e.g., the height (H) of the fired staple 608a in FIG. 7). In one embodiment, the uncompressed height of the scaffold 604 can be about 10% taller, about 20% taller, about 30% taller, about 40% taller, about 50% taller, about 60% taller, about 70% taller, about 80% taller, about 90% taller, or about 100% taller than the fired height of the staples 608. In certain embodiments, the uncompressed height of the scaffold 604 can be over 100% taller than the fired height of the staples 608, for example.

Figure 7:
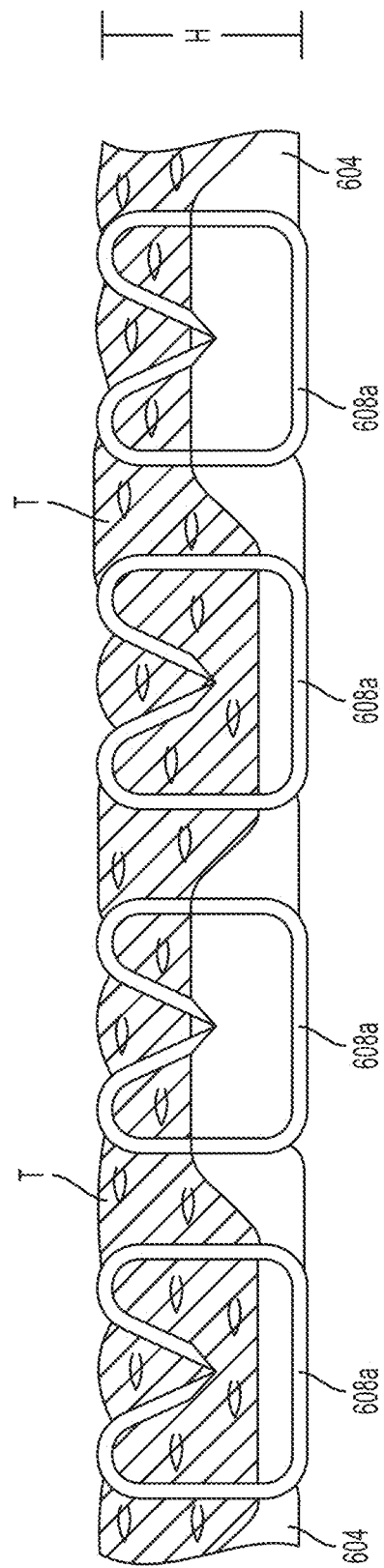
FIG. 7 is a schematic illustrating the scaffold of FIG. 6 when stapled to tissue.

The scaffold 604 can be releasably mated to the outer surface 612 of the cartridge deck 606. As shown in FIG. 7, when a staple is fired, tissue (T) and a portion of the scaffold 604 is captured by the fired (formed) staple 608a. The fired staple 608a defines the entrapment area therein, as discussed above, for accommodating the captured scaffold 604 and tissue (T). The entrapment area defined by the fired staple 608a is limited, at least in part, by a height (H) of the fired staple 608a. For example, the height of a fired staple 608a can be about 0.130 inches or less. In some embodiments, the height of a fired staple 608a can be from about 0.025 inches to 0.130 inches. In some embodiments, the height of a fired staple 608a can be from about 0.030 inches to 0.100 inches.

As described above, the scaffold 604 can be compressed within a plurality of fired staples whether the thickness of the tissue captured within the staples is the same or different within each staple. In at least one exemplary embodiment, the staples within a staple line, or row, can be deformed such that the fired height is about 2.75 mm, for example, where the tissue (T) and the scaffold 604 can be compressed within this height. In certain instances, the tissue (T) can have a compressed height of about 1.0 mm and the scaffold 604 can have a compressed height of about 1.75 mm. In certain instances, the tissue (T) can have a compressed height of about 1.50 mm and the scaffold 604 can have a compressed height of about 1.25 mm. In certain instances, the tissue (T) can have a compressed height of about 1.75 mm and the scaffold 604 can have a compressed height of about 1.00 mm. In certain instances, the tissue (T) can have a compressed height of about 2.0 mm and the scaffold 604 can have a compressed height of about 0.75 mm. In certain instances, the tissue (T) can have a compressed height of about 2.25 mm and the scaffold 604 can have a compressed height of about 0.50 mm. Accordingly, the sum of the compressed heights of the captured tissue (T) and scaffold 604 can be equal, or at least substantially equal, to the height (H) of the fired staple 608a.

As discussed in more detail below, the structure of the scaffold can be configured such that when the scaffold and tissue are captured within the fired staple, the scaffold can apply a stress that can withstand the pressure of circulating blood through tissue. High blood pressure is typically considered 210 mmHg, and therefore it would be desirable for the scaffold to apply a stress to the tissue that is equal to or greater than 210 mmHg (e.g., 3 gf/mm$^2$) for a predetermined time period (e.g., 3 days). As such, in certain embodiments, the scaffold can be configured to apply a stress of at least about 3 gf/mm$^2$ to the captured tissue for at least 3 days. The scaffold is in a tissue deployed state when the scaffold is stapled to tissue in vivo. In one embodiment, the applied stress can be about 3 gf/mm$^2$. In another embodiment, the applied stress can be greater than 3 gf/mm$^2$. In yet another embodiment, the stress can be at least about 3 gf/mm$^2$ and applied to the captured tissue for more than 3 days. For example, in one embodiment, the stress can be at least about 3 gf/mm$^2$ and applied to captured tissue for about 3 days to 5 days.

In order to design a scaffold that is configured to apply a stress of at least about 3 gf/mm$^2$ to the captured tissue for a predetermined time, one can use the principles of Hooke's law (F=kD). For example, when the force (stress) to be applied to the captured tissue is known, one can design a scaffold to have a stiffness (k). The stiffness can be set by tuning the materials and/or the geometry of the scaffold (e.g., the type and/or diameter of the fibers and/or the interconnectivity of the fibers). Further, one can design the scaffold to have a maximum amount of compression displacement for a minimum thickness of tissue, e.g., 1 mm, and therefore the length of displacement D can be the combination of a minimum thickness of tissue, e.g., 1 mm, plus a thickness of the tissue when stapled to tissue for a given max staple height, e.g., 2.75 mm.

By way of example, in one embodiment, a scaffold can be structured to have a height that is greater than a maximum formed stapled height of 2.75 mm and to compress to a height of 1.75 mm when stapled to tissue having a minimum thickness of 1 mm. Therefore, the scaffold can vary in compressibility to maintain a constant length of displacement D such that the stiffness (k) and total thickness (D) of captured tissue and scaffold can apply a stress of 3 gf/mm$^2$ to the captured tissue. It should be noted a person of ordinary skill in the art will appreciate that the foregoing formula can be modified to take into account variations in temperatures, e.g., when the adjunct is brought from room temperature to body temperature after implantation.

Additionally, the scaffold can be further developed to provide a substantially continuous stress to the captured tissue (e.g., 3 gf/mm$^2$) for a predetermined time (e.g., 3 days). To achieve this, one would need to take into account the degradation rate of the materials of the scaffold and the rate of tissue ingrowth within the scaffold when designing the scaffold. In doing so, one can design a scaffold such that the stiffness of the scaffold and/or the total thickness of the captured tissue and scaffold do not vary in a way that could effect an applied stress that is less than 3 gf/mm$^2$.

A scaffold is stapled to tissue under various stapling conditions (e.g., tissue thickness, height of formed staple, intra-tissue pressure). Depending on the stapling condition, one can determine an effective amount of stress that the scaffold needs to be able to apply to the tissue to prevent tissue tearing and leakage. For example, in one embodiment, an effective amount of stress is at least about 3 gf/mm$^2$. In order for the scaffold to provide an effective amount of stress to the tissue, the scaffold can be designed to effectively compensate for the various stapling conditions. As such, the scaffold can be tailored to assume different compressed heights when stapled to tissue. As there is a finite range of intra-tissue pressures, tissue thicknesses, and formed staple heights, one can determine appropriate material and/or geometric structures for the scaffold that can be effective in applying a substantially continuous desired stress to the tissue (e.g., 3 gf/mm$^2$) when stapled thereto for a given amount of time (e.g., at least 3 days) over a range of stapling conditions. That is, as described in more detail below, the present scaffolds are formed of compressible materials and geometrically configured so as to allow the scaffold to compress to various heights in predetermined planes when stapled to tissue. Further, this varied response by the scaffold can also allow the scaffold to maintain its application of a continuous desired stress to the tissue when exposed to fluctuations in intra-tissue pressure that can occur when the scaffold is stapled to tissue (e.g., a spike in blood pressure).

The scaffold can have a variety of configurations. For example, in certain embodiments, the scaffold can include at least one knitted layer and at least one support layer. As used herein, "knitted layer" is used synonymously with "knitted zone," and "support layer" is used synonymously with "spacer zone."

FIGS. 8A-8C and 9 illustrate an exemplary embodiment of a scaffold 800 having first and second knitted layers 802, 804 with a support layer 806 disposed therebetween. In this illustrated embodiment, the first knitted layer 802 can be configured to be positioned against tissue and the second knitted layer 804 can be configured to be positioned against a cartridge deck, like cartridge deck 606 in FIG. 6.

As shown, the knitted layers 802, 804 includes fibers 808 of a first type and fibers 810 of a second type, and the support layer 806 includes the second type of fibers 810. In this way, by having the scaffold 800 formed of two different fibers 808, 810 the scaffold can have a variable stiffness profile over time following implantation. For example, the first type of fibers 808 can function as a structural component of the knitted layers 802, 804, and the stiffness profile can be a function of the degradation profile of the first type of fibers 808 and the interaction between the first type of fibers 808 with the second type of fibers 810 in the knitted layers 802, 804.

Further, the knitted layers 802, 804 can be configured such that when the scaffold 800 is attached to a cartridge deck, at least a portion of the first type of fibers 808 are oriented in a direction that is substantially parallel to the cartridge deck. While the first and second type of fibers 808, 810 can have a variety of sizes, in some implementations, the first type of fibers 808 has a fiber diameter that is less than a fiber diameter of the second type of fibers 810.

While the fibers 808, 810 of the knitted layers 802, 804 and of the support layer 806 can either be monofilament or multifilament, in some implementations, the first type of fibers 808 are multifilament fibers and the second type of fibers 810 are monofilament fibers, as shown in FIGS. 8A-8C and 9. As used herein, the term "monofilament fibers" has its own ordinary and customary meaning and can include fibers formed of a single filament. As used herein, the term "multifilament fibers" has its own ordinary and customary meaning and can include fibers formed of two or more filaments that are associated with one another to form a unitary structure. In one embodiment, the multifilament fibers are non-bonded multifilament fibers. As used herein, a "non-bonded multifilament fiber" has its own ordinary and customary meaning and can include an assembly of two or more filaments that are in contact with one another at least one point along their lengths but are not physically attached to one another. Non-limiting examples of non-bonded multifilament fibers include yarn (filaments twisted about one another along their lengths) and tow (filaments not twisted about one another along their lengths).

The multifilament fibers can have a variety of configurations. For example, in some implementations, each multifilament fiber includes from about 6 to 40 filaments. In one aspect, each multifilament fiber includes from about 14 to 28 filaments. The increased surface area and voids that exist between the filaments of the multifilament fibers can facilitate improved tissue ingrowth within the scaffold (see e.g., Example 2).

The multifilament fibers can have a variety of sizes. For example, each multifilament fiber can have an average diameter of about 0.02 mm to 0.2 mm, of about 0.05 mm to 0.2 mm, or of about 0.15 mm to 0.2 mm. In some implementations, each filament of the multifilament fibers has a diameter that is less than a fiber diameter of the monofilament fibers. For example, where the knitted layers 802, 804 include first type of fibers that are multifilament fibers and second type of fibers that are monofilament fibers, each filament of the multifilament fibers can have a diameter that is about 1/5 to 1/20 the diameter of the monofilament fibers. In certain embodiments, each filament of the multifilament fibers can have a diameter that is about 1/10 the diameter of the monofilament fibers.

The multifilament fibers can be formed of filaments formed of the same material or filaments of different materials. For example, in some implementations, the multifilament fibers can include first filaments of a first material and second filaments of a second material. In one embodiment, the second material degrades at a faster rate than a degradation rate of the first material. In this way, the degradation of the second material can activate, and thus encourage accelerated attraction of, macrophages and accelerate the inflammation phase of healing while not substantially affecting the variable stiffness profile of the scaffold over time following implantation. The activation of macrophages can in turn cause increases in myofibroblast population and neovascularization. Further, the degradation of the second material can encourage tissue ingrowth within the scaffold. The first material, for example, can be at least one of poly-L-lactic acid, a copolymer of glycolide and L-lactide, a copolymer of glycolic acid and lactic acid, poly(lactic-co-glycolic acid), poly(lactic acid), polyglycolide, and a copolymer of glycolide, caprolactone, trimethylene carbonate, and lactide. Non-limiting examples of suitable first materials can be formed of polyglactin 910, Lactomer™ 9-1, 75:25 or 50:50 lactic acid/glycolic acid, Polygytone™ 6211, or Caprosyn™. The second material, for example, can be a copolymer of glycolide and L-lactide, such as Vicryl Rapide™.

While the multifilament fibers can include the second filaments at various percentage ranges, in some implementations, the multifilament fibers can each include second filaments at a range of about 15% to 85% or at a range of about 25% to 45%. The second filaments can have various fiber diameters. For example, in some implementations, the second filaments can have a fiber diameter from about 0.0005 mm to 0.02 mm. In one embodiment, the second filaments have a fiber diameter of about 0.015 mm.

The monofilament fibers can have a variety of sizes. For example, the monofilaments can have a diameter of about 0.2 mm to 0.35 mm. In some implementations, the monofilament fibers can each have a diameter that is less than an average diameter of the multifilament fibers. The average diameter (D) of a multifilament fiber can be calculated using the following formula:

$$D = \sqrt{\frac{4W}{N\rho\pi}}$$

where, $W$ = weight of multifilament fiber (fiber bundle) per unit length $N$ = number of filaments $\rho$ = density of fiber.

While the first and second type of fibers 808, 810 can have various glass transition temperatures, in some implementations, the first type of fibers 808 have a first glass transition temperature and the second type of fibers 810 have a second glass transition temperature that is less than the first glass transition temperature. For example, the first glass transition temperature can be greater than the second glass transition temperature by at least about 30 degrees C. In other exemplary embodiments, the first glass transition temperature can be greater than the second glass transition temperature by at least about 45 degrees C. A difference in glass transition of the first and second types of fibers 808, 810 can further facilitate a secure attachment of the scaffold to the cartridge deck without adversely affecting the structural integrity of the scaffold.

As discussed above, a portion of the scaffold is captured with tissue within the fired staple and therefore it is desirable that the scaffold be formed of suitable bioabsorbable materials. As such, the first and second type of fibers 808, 810 can each be formed of a variety of absorbable materials. Non-limiting examples of suitable materials for the first type of fibers include at least one of poly-L-lactic acid, a copolymer of glycolide and L-lactide, a copolymer of glycolic acid and lactic acid, poly(lactic-co-glycolic acid), poly(lactic acid), polyglycolide, and a copolymer of glycolide, caprolactone, trimethylene carbonate, and lactide. For example, the first type of fibers can be formed of polyglactin 910, Lactomer™ 9-1, 75:25 or 50:50 lactic acid/glycolic acid, Polygytone™ 6211, or Caprosyn™. Non-limiting examples of suitable materials for the second type of fibers include at least one of polydioxanone, a copolymer of polydioxanone and polyglycolide, a copolymer of lactide and polycaprolactone), a copolymer of glycolide, dioxanone, and trimethylene carbonate, poly(trimethylene carbonate), polyhydroxyalkanoate, and polyglyconate. For example, the second type of fibers can be formed of 92:8 polydioxanone/Polyglycolide, 25:75 lactide/polycaprolactone, Glycomer™ 631, or Maxon™. In one embodiment, the first type of fibers is formed of polyglactin 910 and the second type of fibers is formed of polydioxanone.

In some embodiments, the first type of fibers 808 can be coated with a bioabsorbable polymeric material. In this way, the glass transition temperature of the first type of fibers 808 can be modified, e.g., by either increasing or decreasing the glass transition compared to the glass transition temperature of the base material of the first type of fibers, which in certain instances may be desirable for attaching the scaffold to the cartridge deck. For example, decreasing the glass transition temperature of the first type of fibers 808 can provide a more secure attachment of the scaffold 800 to a cartridge deck, like cartridge deck 606 in FIG. 6, and/or enhance the conformability of the scaffold 800 to the cartridge deck and, when cooled, maintain a suitable shape. Non-limiting examples of suitable coating materials include polydioxanone or 25:75 lactide/polycaprolactone.

While the knitted layers 802, 804 can each have various knitted patterns, in some implementations, like in FIGS. 8A-8C and 9, the knitted layers 802, 804 can each have a Rachel knit pattern (e.g., as described in Example 1 below). A person skilled in the art will appreciate that the knitted layers of the scaffold can take the form of other warp knitted patterns.

As shown in FIGS. 8A-8C and 9, the second type of fibers 810 interconnect with the first type of fibers 808 of the first and second knitted layers 802, 804 in a manner in which the first and second fibers are non-fixedly attached and slidably interconnected. As such, in this illustrated embodiment, the first and second type of fibers 808, 810 can move relative to each other, thereby allowing for movement and for expansion in the x-direction (e.g., stretch) and the y-direction (e.g., compression). Additionally, the interconnection between the first and second type of fibers 808, 810 can affect, at least in part, the stiffness of the scaffold 800. For example, the tighter the interconnection, the stiffer the scaffold 800.

Further, as shown in the FIGS. 8A-8C and 9, the first and second knitted layers 802, 804 each include a plurality of openings 812 formed therein. The openings 812 of the first and second knitted layers 802, 804 each have a perimeter formed of the first and second types of fibers 808, 810. The openings 812 of the second knitted layer 804 can have a size that is less than about ¼ of a width of a crown of a staple, like staple 406 in FIG. 5. As such, in some implementations, the crown of the fired staple can span over at least four openings 812 in the second knitted layer 804. In one embodiment, the openings 812 can have a size that is about ⅛ of the width of the crown. While the crown of a staple can have a variety of widths, in some implementations, the width of the crown can be about 0.080 inches to 0.140 inches. In one embodiment, the width of the crown is about 0.12 inches.

The plurality of openings 812 in the first and second knitted layers 802, 804 can have a variety of sizes. For example, the plurality of openings 812 in the second knitted layer 804 can have a diameter from about 0.002 inches to 0.1 inches. As used herein, "diameter" of an opening is the largest distance between any pair of vertices of the opening.

As discussed above and shown in FIGS. 8A-8C and 9, the scaffold 800 includes a support layer 806 that is positioned between the first and second knitted layers 802, 804. The support layer 806 is non-fixedly attached to first and second knitted layers 802, 804. The support layer 806 can be configured such that when the scaffold 800 is attached to a cartridge deck, like cartridge deck 606 in FIG. 6, at least a portion of the second type of fibers 810 of the support layer 806 are oriented in a direction that is substantially non-parallel to the cartridge deck. While the support layer 806 is shown in FIGS. 8A-8C and 9, to include only the second type of fibers 810, which in this exemplary embodiment, are monofilaments, it is also contemplated herein that the support layer 806 can include additional types of fibers, including, for example, the first type of fibers 808.

As shown, the fibers 810 of the support layer 806 are arranged within the support layer 806 to form standing (spacer) fibers 814 and a plurality of voids 816 therebetween. The standing fibers 814 are non-fixedly attached to each other. Further, the standing fibers 814 are non-fixedly and slidably interconnected to the first type of fibers 808 of the first and second knitted layers 802, 804. In some implementations, the plurality of voids 816 can be larger than the plurality of openings 812 in the first and second knitted layers 802, 804.

The standing fibers 814 are configured to bend under force applied to the scaffold 800 (e.g., when stapled to tissue). The resilience of the standing fibers 814 permits, at least in part, the scaffold to compress at various heights to thereby accommodate tissue (T) with tissue portions of different thicknesses. That is, independent of the particular tissue thickness, the sum of the compressed heights of the captured tissue and scaffold within the fired staple can be maintained, and thus can remain equal, or at least substantially equal, to the height of the fired staple. In this way, at least in part, the scaffold 800 can be configured to apply a stress of at least about 3 $gf/mm^2$ to the captured tissue for at least a predetermined period (e.g., at least about 3 days).

Figure 8A:
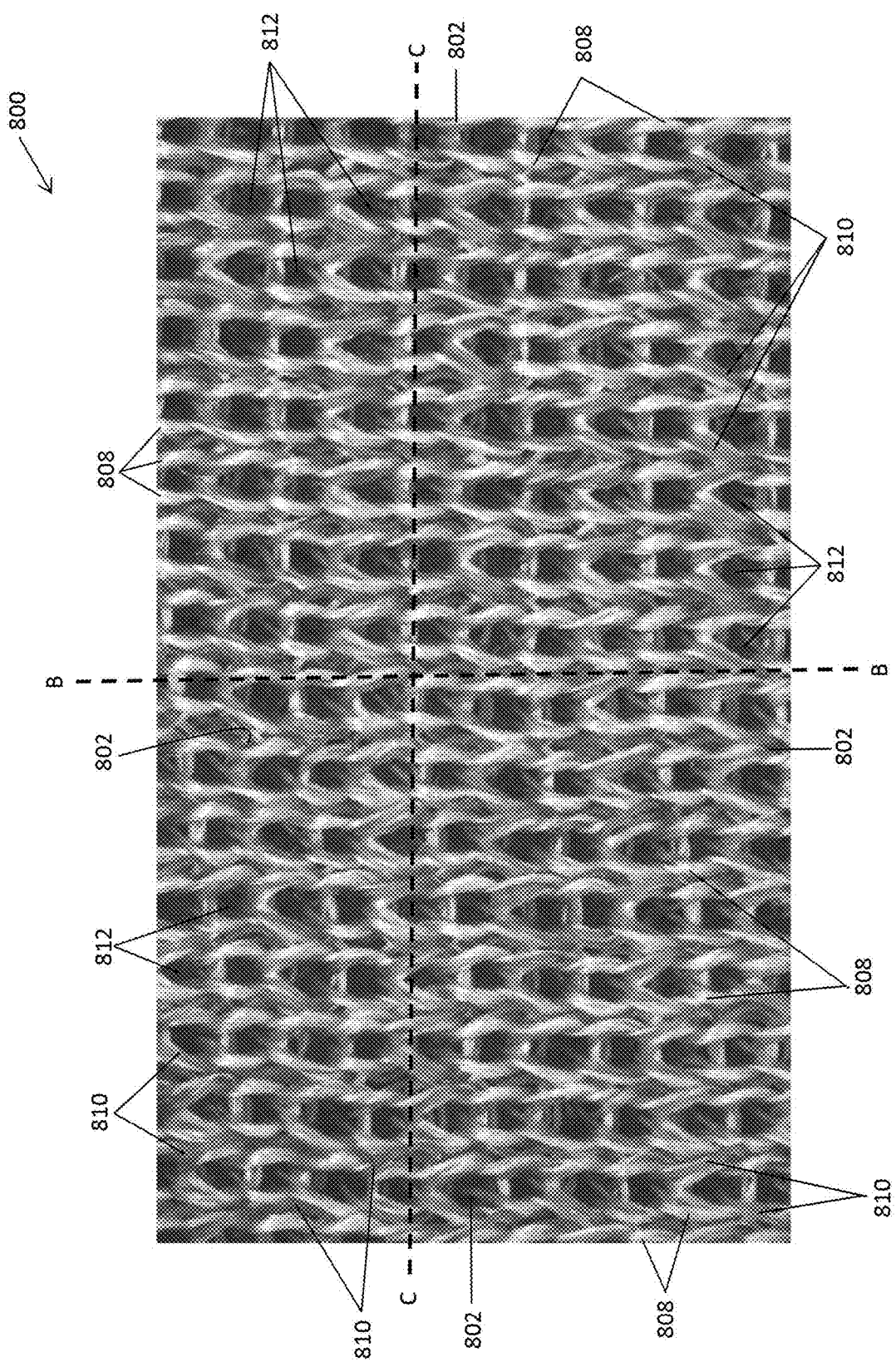
FIG. 8A is a magnified top view of an exemplary embodiment of a scaffold that can be attached to the cartridge deck of the surgical cartridge assembly of FIG. 6.
Figure 9:
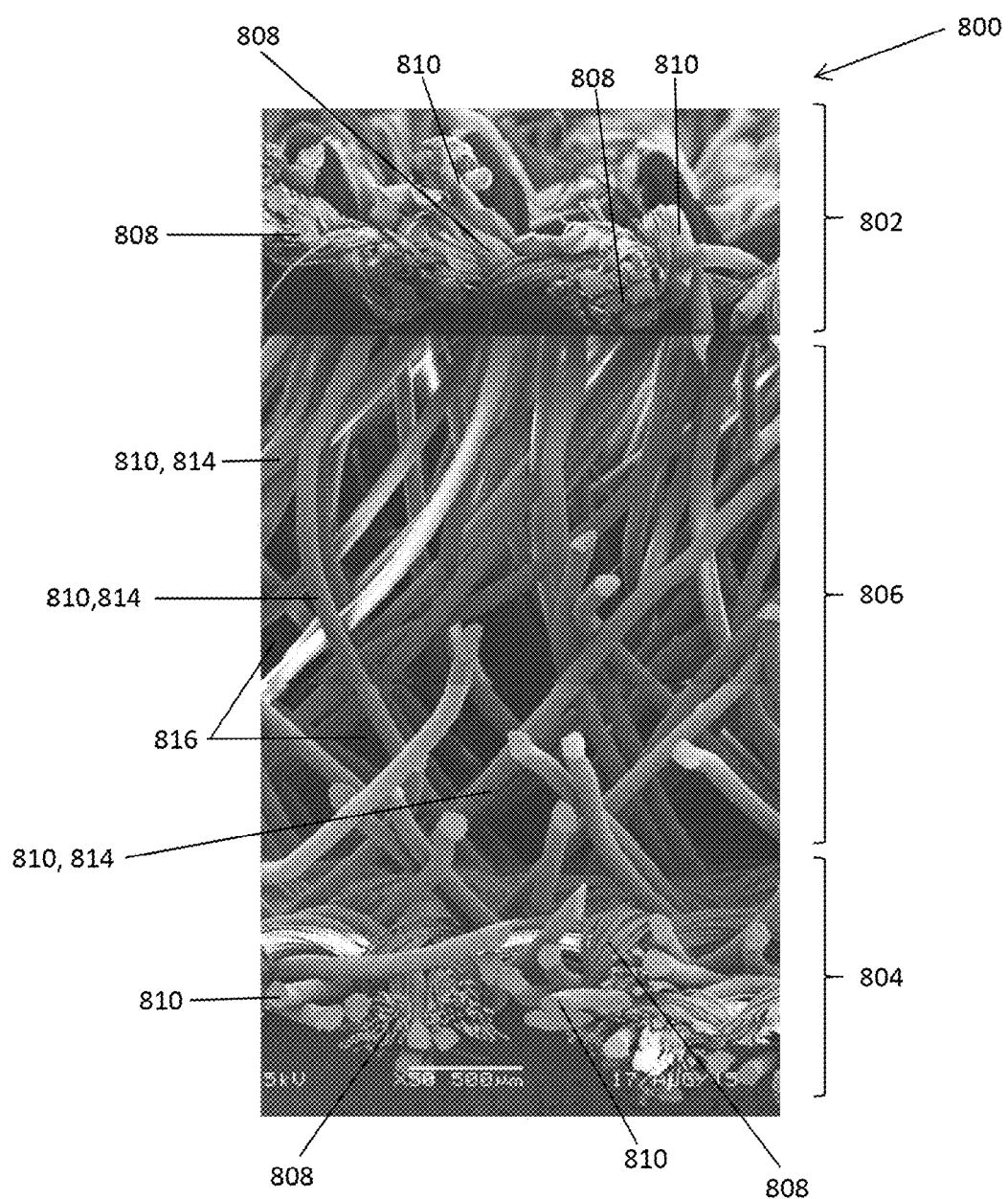
FIG. 9 is a scanning electron micrograph (SEM) image of the scaffold in FIGS. 8A-8C at 500 μm scale.

Generally, the material composition, the height, and/or the transverse cross-sectional area of each standing fiber 814 controls, at least in part, its stiffness or ability to bend under compression which, in turn, controls, at least in part, the compressibility of the scaffold 800. Accordingly, the standing fibers 814 can be configured to tune the compressibility of the scaffold 800 to one or more desired values. For example, while the standing fibers 814 in FIGS. 8B-8C and 9 are of the same material, in some implementations, the support layer 806 can include standing fibers of different materials with different stiffnesses. Alternatively or in addition, in some implementations, the support layer 806 can include standing fibers of different heights and/or transverse cross-sectional areas. In one embodiment, the standing fibers 814 can have a high length-to-diameter ratio, for example, a ratio of about 25:1 to 6:1. In this way, the standing fibers 814 can further encourage tissue ingrowth and cell integration within the implanted scaffold.

The amount of the standing fibers 814 within a certain section of the support layer 806 can also affect, among other things, the compressibility of such section, and thus the compressibility of the scaffold 800. In certain instances, the standing fibers 814 can be strategically concentrated in certain sections of the support layer 806 to provide greater column strength in such sections, for example. In at least one instance, the standing fibers 814 can be concentrated in sections of the support layer 806 that are configured to receive staples when the staples are fired. Alternatively, the standing fibers 814 can be concentrated in sections of the support layer 806 that do not receive staples when the staples are fired.

The ratio of the voids 816 to the standing fibers 814 can vary. In one implementation this ratio can be in the range of at least about 3:1. In other implementations, the ratio of voids 816 to the standing fibers 814 can in the range of at least about 5:1 or of at least about 12:1. Further, at least a portion of the voids 816 in the support layer 806 can each have a different size. In this way, the variable void sizes throughout the cross-section of the scaffold 800 can promote extracellular remodeling. That is, the variable void sizes can facilitate revascularization as well as mobility of cells within the scaffold 800 when the scaffold is implanted, thereby encouraging both tissue and cellular ingrowth. Further the variable void sizes can also facilitate extraction of byproducts and cellular waste from the implanted scaffold, and thus the implantation site.

In some embodiments, the scaffold 800 can also include a porous layer interconnected to the second knitted layer 804. In this way, when the scaffold 800 is attached to a cartridge deck, like cartridge deck 606 in FIG. 6, the porous layer would be positioned between the cartridge deck and the second knitted layer 804. In one embodiment, the porous layer is fused or bonded to the second knitted layer 804. The porous layer can be formed of a material having a lower glass transition temperature than the fibers 808, 810 of the scaffold 800. It is also contemplated herein that the porous layer can be formed of a material having the same or a higher glass transition temperature than at least one of the fibers 808, 810 of the scaffold 800. The porous layer can have a thickness that is less than about 0.003 inches. In one embodiment, the porous layer has a thickness that is less than about 0.001 inches. The porous layer can also include pores that are greater than about 0.0005 inches in diameter. For example, in some implementations, the pores can vary in size from about 0.0005 inches to about 0.001 inches. Further, in some implementations, the pores can make up at least 50% of the surface area of the layer.

The scaffolds described herein, like scaffold 800 in FIGS. 8A-8C and 9, can be manufactured using any suitable methods. For example, in one embodiment, the method can include forming a first knitted layer, forming a second knitted layer, and interknitting spacers with the first and second knitted layers. The first and second knitted fibers can comprise fibers of a first polymer. The first knitted layer can be configured to mate with a cartridge deck. Interknitting the spacer fibers with the first and second knitted layers can connect the first and second knitted layers together in a spaced parallel relation. As used herein, a "spaced parallel relation" means that the first and second layers extend within planes that are distanced from and substantially parallel with one another. The spacer fibers can be formed of only a second polymer that is different than the first polymer. The first polymer fibers can have a diameter that is different than a diameter of the second polymer fibers. The spacer fibers can be integrated with and extending between the first and second knitted layers. The method can also include annealing the first and second knitted layers interknitted with the spacer fibers.

The interknitting of the spacer fibers with the first and second knitted layers can form a support layer therebetween. The formation of the first knitted layer can include knitting the first polymer fibers according to a predetermined pattern. The formation of the second knitted layer can include knitting the first polymer fibers according to a predetermined pattern. While the knitted layers can each have various knitted patterns, in some implementations, the knitted layers can each have a Rachel knit pattern (e.g., as described in Example 1 below). A person skilled in the art will appreciate that the knitted layers of the scaffold can take the form of other warp knitted patterns.

Figure 12A:
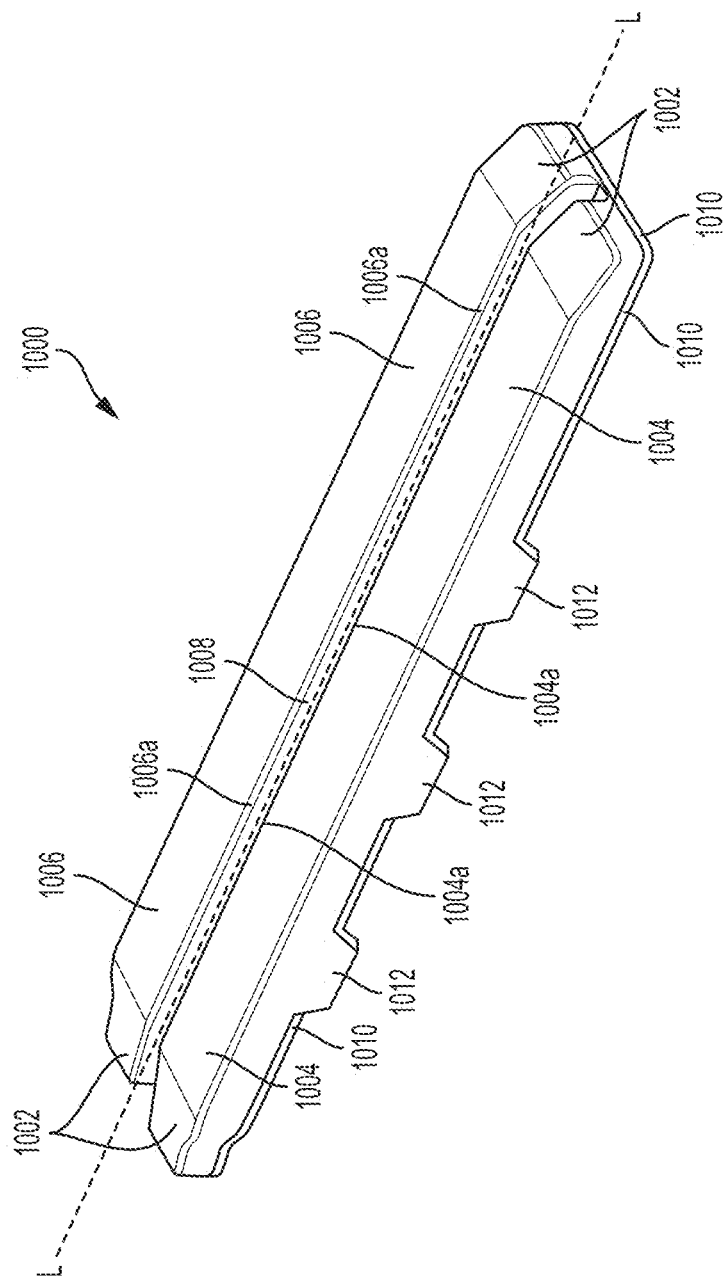
FIG. 12A is a perspective view of another exemplary embodiment of a scaffold.
Figure 12B:
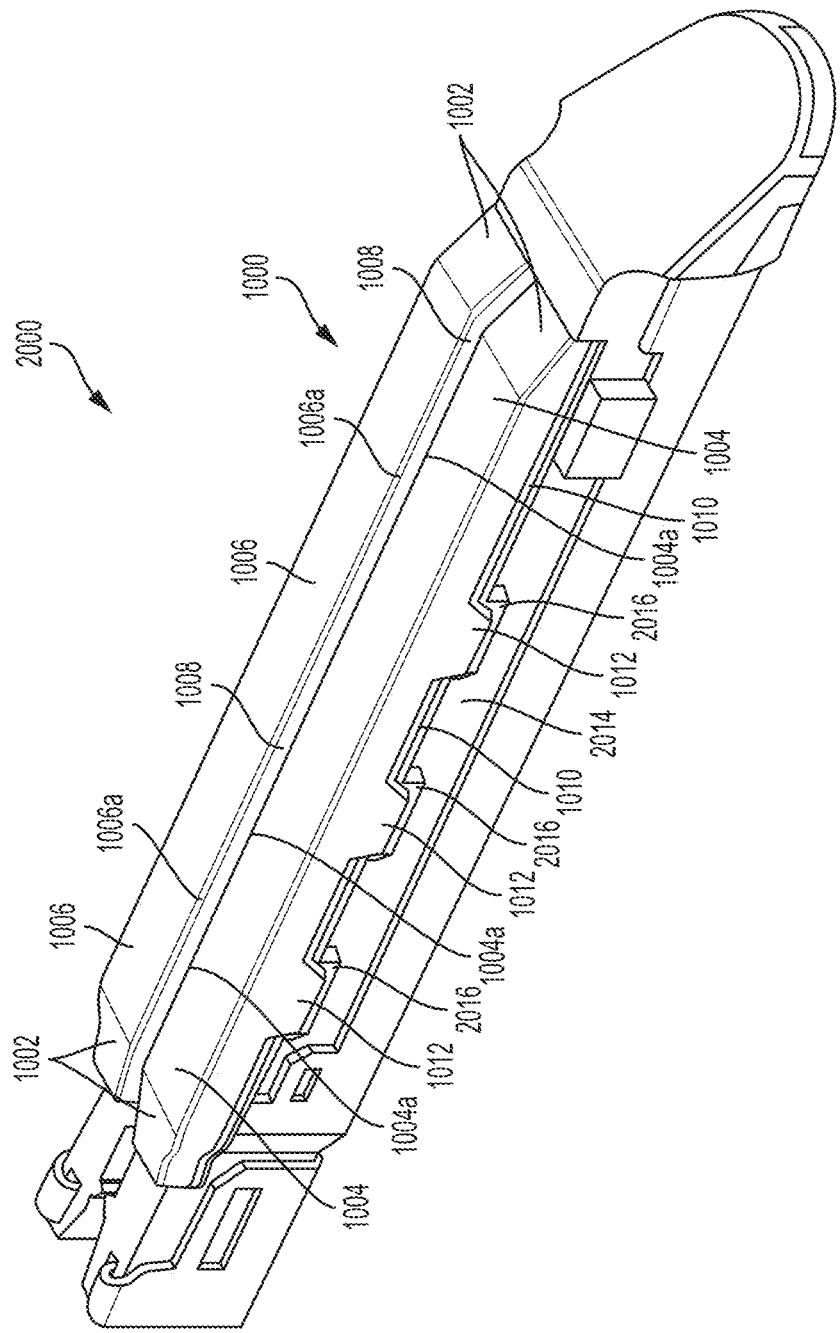
FIG. 12B is another exemplary embodiment of a staple cartridge assembly having the scaffold shown in FIG. 12A attached to a cartridge deck.
Figure 13:
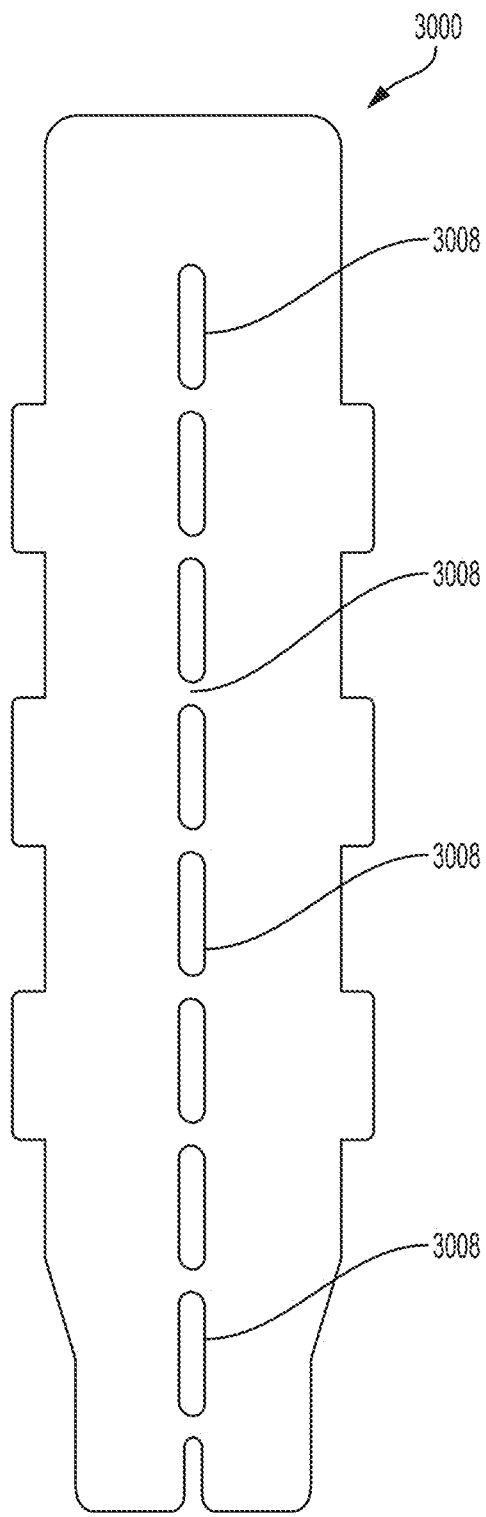
FIG. 13 is a bottom view of another exemplary embodiment of a scaffold.

FIG. 12A illustrates another exemplary embodiment of a scaffold 1000. Aside from the differences described in detail below, the scaffold 1000 can be similar in construction to the scaffold 800 (FIGS. 8A-8C and 9) and is therefore not described in detail herein. In this embodiment, the scaffold 1000 includes a first knitted layer 1002 having a first portion 1004 and a second portion 1006, each having outer and inner edges. The inner edges 1004a, 1006a define a channel 1008 that extends along the longitudinal axis (L) of the scaffold 1000. The channel 1008 is configured to receive a cutting member, such as a knife. As shown in FIG. 12B, the channel 1008 does not extend completely through the scaffold 1000. In particular, the channel 1008 does not extend through the second knitted layer 1010. In this way, the scaffold 1000 is configured to have sufficient structural integrity to thereby be effectively manipulated and attached to a cartridge deck, like cartridge deck 2014 in FIG. 12B. In another embodiment, as shown in FIG. 13, the scaffold 3000 can have a channel 3008 that is perforated. In use, when the cutting member is initially fired and travels along the scaffold 1000, the cutting member cuts through the second knitted layer 1010, thereby separating the scaffold 1000 into two pieces.

Further, as shown in FIG. 12A, the scaffold 1000 includes flanges 1012 that are configured to mate with recessed channels, like recessed channels 2016 of cartridge deck 2014 in FIG. 12B, as further described below. While FIG. 12A illustrates the scaffold 1000 having flanges 1012 at one side of the scaffold 1000, there are additional flanges 1012 positioned at the opposite side of the scaffold 1000. A person skilled in the art will appreciate that the number and placement of flanges 1012 are not limited to what is shown in FIG. 12A. While the flanges 1012 can be made of a variety of materials, in some implementations, as shown in FIG. 12A, the flanges 1012 are an extension of the second knitted layer 1010. In other embodiment, the flanges 1012 can be formed of different material and formed in-line or offline with the other components of the scaffold 1000. A person skilled in the art will appreciate that the flanges can be formed of the same or different materials than that of the first and/or second knitted layers of the scaffold and can be attached thereto by any suitable method.

FIG. 12B illustrates another exemplary embodiment of a staple cartridge assembly 2000. Aside from the differences described in detail below, the staple cartridge assembly 2000 can be similar to staple cartridge assembly 600 (FIG. 6) and is therefore not described in detail herein. Further, for purposes of simplicity, certain components of the staple cartridge assembly 2000 are not illustrated in FIG. 12B.

The staple cartridge assembly 2000 includes the scaffold 1000 in FIG. 12A attached to a cartridge deck 2014 having recessed channels 2016. The scaffold 1000 can be attached to the cartridge deck using any suitable methods, as described in more detail below. As shown, the recessed channels 2016 are configured to receive the flanges 1012 such that the flanges 1012 can attach to the side(s) of the cartridge deck. In this way, the scaffold 1000 can be more securely attached to the cartridge deck 2014, thereby preventing undesired movement of the scaffold 1000 during use.

The scaffolds can be applied to a cartridge deck to form a staple cartridge assembly using any suitable method. For example, in some embodiments, the method can include heating a cartridge deck and positioning a scaffold against a surface of the cartridge deck. The scaffold can include first and second type of fibers in which the first type of fibers are predominately present. As used herein, "predominately present" when used to describe the amount of particular fibers in a layer means an amount that is greater than 50% of the total amount fibers within that layer. The first type of fibers can have a first glass transition temperature and the second type of fibers can have a second glass transition temperature that is less than the first glass transition temperature. The cartridge deck can be heated to a temperature of at least the second glass transitions temperature. The method can also include cooling the cartridge deck and scaffold applied thereto to a temperature that is less than the second glass transition temperature.

The scaffold can include first and second knitted layers each having the first and second types of fibers and a support layer disposed between the first and second knitted layers. In such instance, the positioning of the scaffold against the surface of the cartridge deck can include placing the first knitted layer against the surface and applying force to the scaffold such that the first knitted layer bonds and conforms to a shape of the surface. The support layer can be formed of the second type of fibers.

The instruments disclosed herein can be designed to be disposed of after a single use, or they can be designed to be used multiple times. In either case, however, the instrument can be reconditioned for reuse after at least one use. Reconditioning can include any combination of the steps of disassembly of the instrument, followed by cleaning or replacement of particular pieces and subsequent reassembly. In particular, the instrument can be disassembled, and any number of the particular pieces or parts of the instrument can be selectively replaced or removed in any combination. Upon cleaning and/or replacement of particular parts, the instrument can be reassembled for subsequent use either at a reconditioning facility, or by a surgical team immediately prior to a surgical procedure. Those skilled in the art will appreciate that reconditioning of an instrument can utilize a variety of techniques for disassembly, cleaning/replacement, and reassembly. Use of such techniques, and the resulting reconditioned instrument, are all within the scope of the present application.

The present teachings may be further understood with reference to the following non-limiting examples.

EXAMPLES

Example 1: Manufacturing of a Scaffold

A sample having two knitted layers and a support layer positioned therebetween was prepared. The two knitted layers were each formed of Vicryl fibers (multifilament fibers of Vicryl) and the support layer was formed of Polydioxanone (PDS) fibers (monofilament fibers of PDS), details of which are provided in Table 1 below.

TABLE 1

Vicryl and Polydioxanone Fiber Information

| Fiber | Fiber Diameter (mils) | Ten (lbf) | Elongation (%) |
| --- | --- | --- | --- |
| 7-0 PDS, dyed | 3.18 | 0.67 | 38.28 |
| 2 ply, 28 denier Vicryl, natural | 1.17 | 0.58 | 20.34 |

The sample was warp knit using a 16 gauge double needle bar Raschel knitting machine with a six guide bar (GB) construction. Each guide bar was individually controlled using a pattern chain, the patterns for which can be found in Table 2 below. PDS was used in the support layer and Vicryl was used for the knitted layers.

TABLE 2

Pattern Chain

| Guide Bars | Guide Bar Movement | Threading | Fiber Used |
| --- | --- | --- | --- |
| 1 | 1-0; 0-0/1-2; 2-2/2-3; 3-3/2-1; 1-1// | Fully | Vicryl |
| 2 | 2-3; 3-3/2-1; 1-1/1-0; 0-0/1-2; 2-2// | Threaded | Vicryl |
| 3 | (1-0; 2-3) × 4// | | PDS |
| 4 | (2-3; 1-0) × 4// | | PDS |
| 5 | 2-2; 2-3/3-3; 2-1/1-1; 1-0/0-0; 1-2// | | Vicryl |
| 6 | 1-1; 1-0/0-0; 1-2/2-2; 2-3/3-3; 2-1// | | Vicryl |

Approximately 6.4 yards of 5 inch wide sample was produced. The sample was scoured with isopropyl alcohol. The sample was placed on a roll, sealed in a nitrogen purged foil bag, and kept under nitrogen flow until further processing.

An approximate 5 inch×5 inch segment of the sample was then annealed using cycle conditions as described in Table 3.

TABLE 3

Cycle Conditions

| $N_2$ Purge | Ramp Up | | Annealing | Cool Down |
| --- | --- | --- | --- | --- |
| Hours/ Temperature (° C.) | Minutes/ Temperature (° C.) | Speed (° C./min) | Hours/ Temperature (° C.) | Minutes/ Temperature (° C.) |
| 1/30 | 90/85 | 0.94/1 | 6/85 | 60/30 |

The annealed sample was then cut to produce approximately 5 mm×10 mm sample scaffolds. One of the scaffold samples was examined by optical microscopy (OM) and SEM. Various OM images of the sample scaffold is shown in FIGS. 8A-8C, and a cross-sectional SEM image of the scaffold sample is shown in FIG. 9.

Example 2: Cellular Ingrowth and Limited Inflammation

Sample scaffolds as prepared in Example 1 were subcutaneously implanted for up to 90 days into rabbits injected with a hematoxylin and eosin stain (H&E) stain. Histopathology images of an implanted scaffold removed at 60 days is illustrated in FIGS. 10A-10B and an implanted scaffold removed at 90 days is illustrated in FIGS. 11A-11B. The white ovals/circles shown in these images are fibers of the scaffold cut either perpendicular or slightly off. As shown, the black boxes illustrate some of the portions of the scaffold in which tissue ingrowth occurred during implantation. Additionally, the arrows in FIGS. 10B and 11B point to inflammatory areas around the fibers, which are indicative of the inflammation phase of healing.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety. Any patent, publication, or information, in whole or in part, that is said to be incorporated by reference herein is incorporated herein only to the extent that the incorporated material does not conflict with existing definitions, statements, or other disclosure material set forth in this document. As such the disclosure as explicitly set forth herein supersedes any conflicting material incorporated herein by reference.

What is claimed is:

1. A method for manufacturing a staple cartridge assembly for use in a surgical instrument, the method comprising:
    heating a cartridge deck; and
    positioning a knitted elastically deformable, bioabsorbable scaffold against a surface of the cartridge deck, the scaffold comprising:
        first and second knitted layers each having fibers of a first type and fibers of a second type, wherein the first type of fibers being predominantly present, wherein the first type of fibers have a first glass transition temperature and the second type of fibers have a second glass transition temperature that is less than the first glass transition temperature; and
        a support layer disposed between the first and second knitted layers, the support layer being formed of the second type of fibers,
    wherein the cartridge deck is heated to a temperature of at least the second glass transition temperature.

2. The method of claim 1, further comprising cooling the cartridge deck and scaffold applied thereto to a temperature that is less than the second glass transition temperature.

3. The method of claim 1, wherein the first glass transition temperature is greater than the second glass transition temperature by at least about 30 degrees C.

4. The method of claim 1, wherein the cartridge deck includes a plurality of staples with each staple partially extending from the surface of the cartridge deck.

5. The method of claim 1, wherein the positioning of the scaffold against the surface of the cartridge deck comprises placing the first knitted layer against the surface and applying force to the scaffold such that the first knitted layer bonds and conforms to a shape of the surface.

6. The method of claim 1, wherein the surface of the cartridge deck includes one or more attachment features that are configured to enhance attachment of the scaffold to the cartridge deck.

* * * * *